United States Patent
Hediger et al.

(10) Patent No.: US 7,078,178 B2
(45) Date of Patent: Jul. 18, 2006

(54) METHODS OF ALTERING CALCIUM TRANSPORT

(75) Inventors: Matthias A. Hediger, 74 Edmunds Rd., Wellesley, MA (US) 02481; Edward M. Brown, Milton, MA (US); Ji-Bin Peng, Boston, MA (US)

(73) Assignee: Matthias A. Hediger, Wellesley, MA (US)

( * ) Notice: Subject to any disclaimer, the term of this patent is extended or adjusted under 35 U.S.C. 154(b) by 353 days.

(21) Appl. No.: 10/420,637

(22) Filed: Apr. 22, 2003

(65) Prior Publication Data

US 2003/0211613 A1 Nov. 13, 2003

Related U.S. Application Data

(60) Continuation of application No. 10/328,091, filed on Dec. 23, 2002, which is a division of application No. 09/350,457, filed on Jul. 9, 1999, now Pat. No. 6,534,642.

(51) Int. Cl.
*G01N 33/52* (2006.01)
*C07K 14/00* (2006.01)
*C07H 21/04* (2006.01)

(52) U.S. Cl. ............... 435/7.21; 435/6; 435/7.1; 435/69.1; 435/235.1; 435/325; 435/375; 435/32.01; 530/350; 536/23.1

(58) Field of Classification Search ............ 435/6, 435/7.21, 7.1, 69.1, 375, 172.3, 235.1, 325, 435/320.1; 530/300, 350, 386; 514/44; 536/23.1, 23.5, 24.5

See application file for complete search history.

(56) References Cited

OTHER PUBLICATIONS

Colbert et al., "OSM-9, A Novel Protein with Structural Similarity to Channels, Is Required for Olfaction, Mechanosensation, and Olfactory Adaptation in *Caenorhabditis elegans*," *The Journal of Neuroscience*, 17(21):8259-8269 (1997).
Hoenderop et al., J. Biol. Chem., 274, pp. 8375-8378, 1999.
Lee et al. "EST210872 Normalized Rat Brain, Bento Soares Rattus sp. cDNA Clone RBRBS54 3' End, mRNA Sequence," Database EMBL: Accession No. AI101583, Oct. 8, 1998, XP000960319 ISSN: 0021-9258.
Peng et al., "Molecular Cloning and Characterization of a Channel-like Transporter Mediating Intestinal Calcium Absorption," *J. Biol. Chem.*, 274(32):22739-22746, 1999.
Peng et al., "CaT1 Expression Correlates with Tumor Grade in Prostate Cancer", Biochemical and Biophysical Research Communications, 282, pp. 729-734, 2001.
Romero et al., Methods Enzymol., 296, pp. 17-52, 1998.
Copy of Written Opinion from PCT/US00/17932, Jul. 10, 2001, 7 pages.

*Primary Examiner*—Janet L. Andres
*Assistant Examiner*—Nirmal S. Basi
(74) *Attorney, Agent, or Firm*—Goodwin Procter LLP

(57) ABSTRACT

Methods of altering transmembrane calcium transport by altering expression of a calcium-transport protein are described.

21 Claims, 11 Drawing Sheets

♦ PKC site   ★ PKA site   ✦ Glycosylation site
ANK REP: ankyrin repeat   TM: transmembrane domain Human CaT1 Primary Structure (SEQ ID NO:2)

```
  1  MGLSLPKEKG LILCLWSKFC RWFQRRESWA QSRDEQDLLQ QKRIWESPLL LAAKDNDVQA
 61  LNKLLKYEDC KVHHRGAMGE TALHIAALYD NLEAAMVLME AAPEL VFEPM TSELYEGQTA
                           ─────────────────────────    ────────
                                    ANK REP 1
121  LHIAVVNQNM NLVRALLARR ASVSARATGT AFRRSPCNLI YFGEHPLSFA ACVNSEEIVR
     ──────────────────────────────                 ──────────────────
                                                         ANK REP 3
           ★                    ♦
181  LLIEHGADIR AQDSLGNTVL HILILQPNKT FACQMYNLLL SYDRHGDHLQ PLDLVPNHQG
     ─────────────────
241  LTPFKLAGVE GNTVMFQHLM QKRKHTQWTY GPLTSTLYDL TEIDSSGDEQ SLLELIITTK
                                                                 ♦ ♦
301  KREARQILDQ TPVKELVSLK WKRYGRPYFC MLGAIYLLYI ICFTMCCIYR PLKPRTNNRT
     ─────────                  ──── ────────────────────
                                         TM 1                 ✦
361  SPRDNTLLQQ KLLQEAYMTP KDDIRLVGEL VTVIGAIIIL LVEVPDIFRM GVTRFFGQTI
     ─────────                        ──────────────────────────────
                                                TM 2
421  LGGPFHVLII TYAFMVLVTM VMRLISASGE VVPMSFALVL GWCNVMYFAR GFQMLGPFTI
     ──────────────────────────────   ──────────────────────────────
                 TM 3                              TM 4
```

FIG. 3A

| FIG. 3A |
|---|
| FIG. 3B |

FIG. 3

```
481  MIQKMIFGDL MRFCWLMAVV ILGFASAFYI IFQTEDPEEL GHFYDYPMAL FSTFELFLTI
                                                                Pore
                             TM 5
541  IDGPANYNVD LPFMYSITYA AFAIIATLLM LNLLIAMMGD THWRVAHERD ELWRAQIVAT
                                           TM 6
601  TVMLERKLPR CLWPRSGICG REYGLGDRWF LRVEDRQDLN RQRIQRYAQA FHTRGSEDLD 661  KDSVEKLELG CPFSPHLSLP MPSVSRSTSR SSANWERLRQ GTLRRDLRGI INRGLEDGES
                                           ◆          ◆
721  WEYQI
```

FIG. 3B

◆ PKC site     ★ PKA site     ✦ Glycosylation site
ANK REP: ankyrin repeat     TM: transmembrane domain Rat CaT1 Primary Structure (SEQ ID NO:4)

```
  1  MGWSLPKEKG LILCLWNKFC RWFHRRESWA QSRDEQNLLQ QKRIWESPLL LAAKENNVQA
                                                  ─────────────────
                                                       ANK REP 1
 61  LIKLLKFEGC EVHQKGAMGE TALHIAALYD NLEAAMVLME AAPELVFEPM TSELYEGQTA
     ──────────────────                           ────               
          ★                                                          
                                       ANK REP 2
121  LHIAVINQNV NLVRALLARG ASVSARATGS VFHYRPHNLI YGEHPLSFA ACVGSEEIVR
     ────────────────────────────────            ──────────────────
                     ◆                                 ANK REP 4
181  LLIEHGADIR AQDSLGNTVL HILILQPNKT FACQMYNLLL SYDGGDHLKS LELVPNNQGL
     ──────────────
       ANK REP 3
241  TPFKLAGVEG NIVMFQHLMQ KRKHIQWTYG PLTSTLYDLT EIDSSGDDQS LLELIVTTKK
                                                                 ◆ ◆
301  REARQILDQT PVKELVSLKW KRYGRPYFCV LGAIYVLYLI CFTMCCVYRP LKPRITNRTN
                 ◆                    ───────────────────────       ✦
                                               TM 1
361  PRDNTLLQQK LLQEAYVTPK DDLRLVGELV SIVGAVIILL VEIPDIFRLG VTRFFGQTIL
                                      ────────────────────
                                               TM 2
```

FIG. 4A

```
421  GGPFHVIIVT YAFMVLVTMV MRLTNSDGEV VPMSFALVLG WCNVMYFARG FQMLGPFTIM
                                            TM 3                          TM 4
481  IQKMIFGDLM RFCWLMAVVI LGFASAFYII FQTEDPDELG HFYDYPMALF STFELFLTII
                                 TM 5                              Pore
541  DGPANYDVDL PFMYSITYAA FAIATLLML NLLIAMMGDT HWRVAHERDE LWRAQVVATT
                                         TM 6
601  VMLERKLPRC LWPRSGICGR EYGLGDRWFL RVEDRQDLNR QRIRRYAQAF QQQDDLYSED
661  LEKDSGEKLE MARPFGAYLS FPTPSVSRST SRSSTNWDRL RQGALRKDLQ GIINRGLEDG
                                              ♦
721  EGWEYQI
```

FIG. 4B

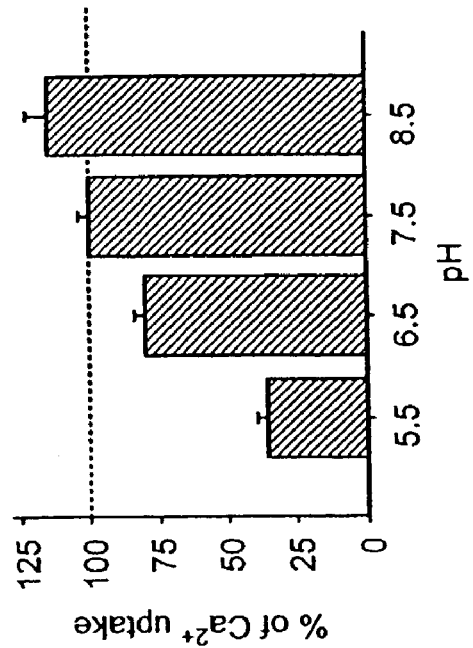
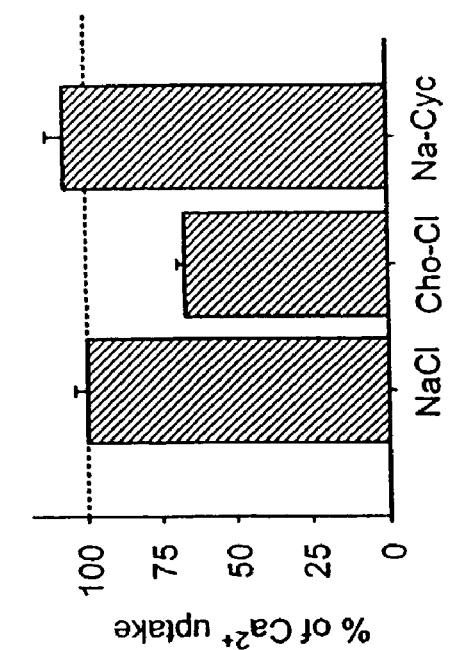
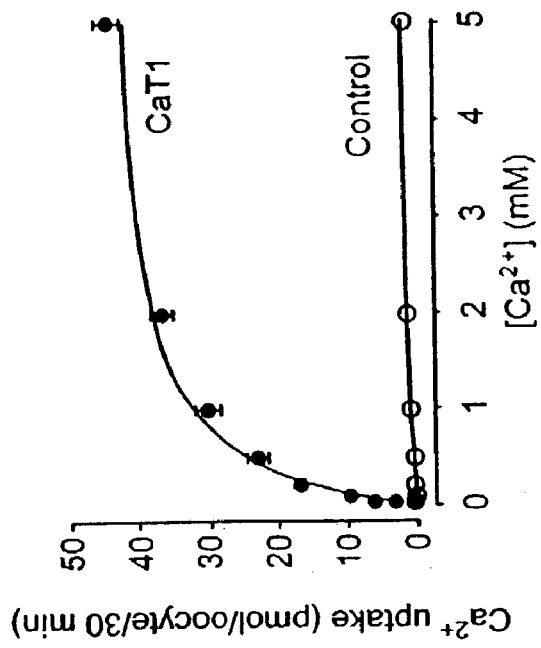
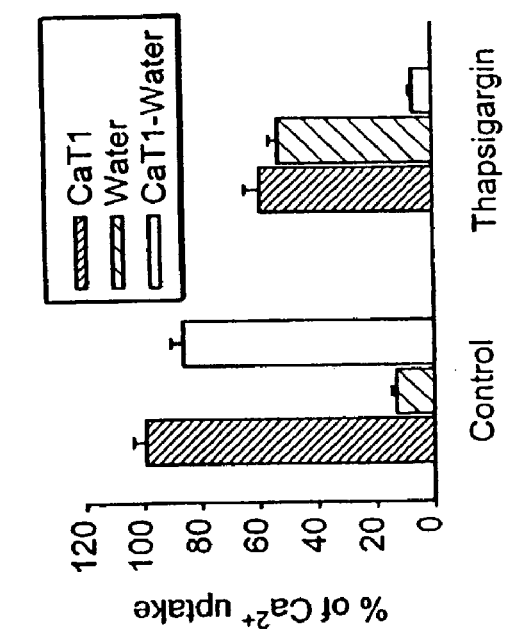
FIG. 5A
FIG. 5B
FIG. 5C
FIG. 5D

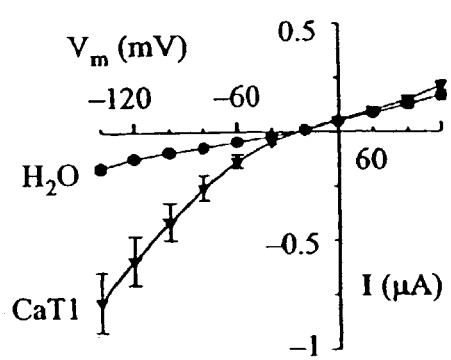
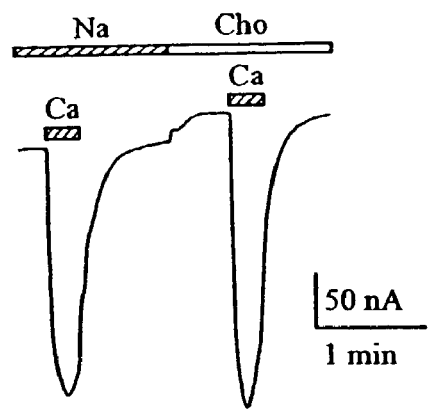
FIG. 7A    FIG. 7B
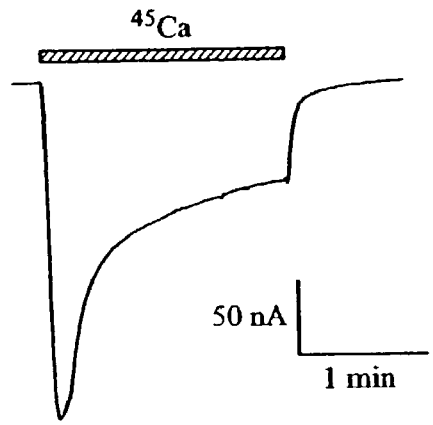
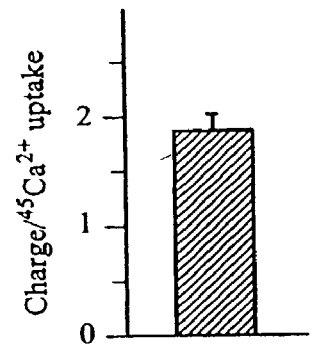
FIG. 8A    FIG. 8B
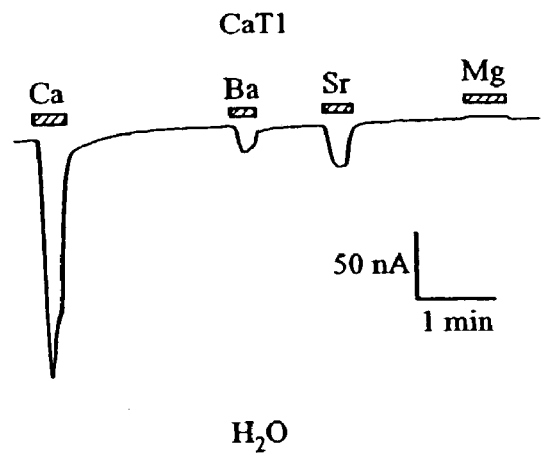
FIG. 9

METHODS OF ALTERING CALCIUM TRANSPORT

REFERENCE TO RELATED APPLICATIONS

This is a continuation of prior application Ser. No. 10/328,091, filed Dec. 23, 2002, which is a divisional of prior application Ser. No. 09/350,457, filed Jul. 9, 1999, now U.S. Pat. No. 6,534,642 B1, the entire disclosures of which are incorporated by reference herein.

FIELD OF THE INVENTION

The present invention relates to transcellular transport of calcium, and in particular to compositions encoding calcium-transport proteins.

BACKGROUND OF THE INVENTION

Calcium is a major component of the mineral phase of bone, and in ionic form plays an important role in cellular signal transduction. In particular, a signaling ligand (the "first messenger") such as a hormone may exert an effect on a cell to which it binds by causing a short-lived increase or decrease in the intracellular concentration of another molecule (the "second messenger"); calcium is known to play the role of first or second messenger in numerous cellular signaling contexts.

Calcium homeostasis in blood and other extracellular fluids is tightly controlled through the actions of calciotropic hormones on bone, kidneys, and intestine. In humans, dietary intake of calcium approximates 500 to 1000 mg/day, and obligatory endogenous losses in stool and urine total about 250 mg/day. On the order of 30% of calcium in the diet must be absorbed to sustain bone growth in children and to prevent postmenopausal bone loss in aging women. To meet the body's need for calcium, the intestines of most vertebrates evolved specialized vitamin D-dependent and -independent mechanisms for ensuring adequate intestinal calcium uptake. Intestinal absorption of $Ca^{2+}$ occurs by both a saturable, transcellular process and a nonsaturable, paracellular pathway. When dietary calcium is abundant, the passive paracellular pathway is thought to be predominant. In contrast, when dietary calcium is limited, the active, vitamin D-dependent transcellular pathway plays a major role in calcium absorption.

The transcellular intestinal-uptake pathway is a multistep process, consisting of entry of luminal $Ca^{2+}$ into an intestinal epithelial cell (i.e., an enterocyte), translocation of $Ca^{2+}$ from its point of entry (the microvillus border of the apical plasma membrane) to the basolateral membrane, followed by active extrusion from the cell. Intracellular $Ca^{2+}$ diffusion is thought to be facilitated by a calcium binding protein, calbindin $D_{9K}$, whose biosynthesis is dependent on vitamin D. The extrusion of $Ca^{2+}$ takes place against an electrochemical gradient and is mainly mediated by Ca-ATPase. The entry of $Ca^{2+}$ across the apical membrane of the enterocyte is strongly favored electrochemically because the concentration of $Ca^{2+}$ within the cell ($10^{-7}$–$10^{-6}$ M) is considerably lower than that in the intestinal lumen ($10^{-3}$ M) and the cell is electronegative relative to the intestinal lumen; as a result, the movement of $Ca^{2+}$ across the apical membrane does not require the expenditure of energy.

The molecular mechanism responsible for entry of $Ca^{2+}$ into intestinal cells has, however, been difficult to characterize. In particular, researchers have disagreed as to whether a transporter or a channel is responsible for this process (although studies have indicated that $Ca^{2+}$ entry is voltage-independent and largely insensitive to classic L-type calcium channel blockers).

DESCRIPTION OF THE INVENTION

Brief Summary of the Invention

The present invention is directed, in a first aspect, toward a membrane protein that functions to transport calcium across cellular membranes. Our data indicate that this protein plays a key role in mediating $Ca^{2+}$ entry into enterocytes as the first step of transcellular intestinal calcium absorption. Expression of the human homologue can be detected in placenta, pancreas, prostate, kidney, the gastrointestinal tract (e.g., esophagus, stomach, duodenum, jejunum colon), liver, hair follicles, and testis, and is also expressed in cancer cell lines (specifically, chronic myelogenous leukemia cell line K-562 and colorectal adenocarcinoma cell line SW480). The rat isoform is expressed in rat intestine (although not in rat kidney). Thus, in contrast to the rat isoform, the human protein may be involved in the absorption/resorption of calcium in both intestine and kidney. Dysfunction of the human protein may be implicated in hyper- and hypocalcemia and calciuria, as well as in bone diseases, leukemia, and cancers affecting the prostate, breast, esophagus, stomach, and colon.

One embodiment of the invention comprises, as a composition of matter, a non-naturally occurring calcium-transport protein. Preferably, the transporter is a polypeptide encoded by a nucleic acid sequence within Seq. I.D. No. 1 or 3. In this context, the term "encoded" refers to an amino-acid sequence whose order is derived from the sequence of the nucleic acid or its complement. The nucleic acid sequence represented by Seq. I.D. No. 1 is derived from human sources. The nucleic acid sequence represented by Seq. I.D. No. 3 is derived from rat.

One aspect of this embodiment is directed toward a transporter having an amino-acid sequence substantially corresponding at least to the conserved regions of Seq. I.D. Nos. 2 or 4. The term "substantially," in this context, refers to a polypeptide that may comprise substitutions and modifications that do not alter the physiological activity of the protein to transport calcium across cellular membranes. The polypeptide represented by Seq. I.D. No. 2 is derived from human sources. The peptide represented by Seq. I.D. No. 4 is derived from rat.

In a second aspect, the invention pertains to a non-naturally occurring nucleic acid sequence encoding a calcium-transport protein. One embodiment of this aspect of the invention is directed toward a transporter having a nucleotide sequence substantially corresponding at least to the conserved regions of Seq. I.D. Nos. 2 or 4. The term "substantially," in this context, refers to a nucleic acid that may comprise substitutions and modifications that do not alter encoding of the amino-acid sequence, or which encodes a polypeptide having the same physiological activity in transporting calcium across cellular membranes. The term "corresponding" means homologous or complementary to a particular nucleic-acid sequence.

As used herein, the term "non-naturally occurring," in reference to a cell, refers to a cell that has a non-naturally occurring nucleic acid or a non-naturally occurring polypeptide, or is fused to a cell to which it is not fused in nature. The term "non-naturally occurring nucleic acid" refers to a portion of genomic nucleic acid, a nucleic acid derived (e.g., by transcription) thereof, cDNA, or a synthetic or semi-synthetic nucleic acid which, by virtue of its origin or isolation or manipulation or purity, is not present in nature, or is linked to another nucleic acid or other chemical agent other than that to which it is linked in nature. The term "non-naturally occurring polypeptide" or "non-naturally occurring protein" refers to a polypeptide which, by virtue of its amino-acid sequence or isolation or origin (e.g., synthetic or semi-synthetic) or manipulation or purity, is not present in nature, or is a portion of a larger naturally occurring polypeptide, or is linked to peptides, functional groups or chemical agents other than that to which it is linked in nature.

A third aspect of the present invention comprises a method of transporting calcium across a cellular membrane having a calcium transporter in accordance herewith. Calcium (in the divalent ionic form) is applied to the cellular membrane under conditions that allow the transporter to transport the calcium.

The cellular membrane can be derived, for example, from placenta, pancreas, prostate, kidney, the gastrointestinal tract (e.g., esophagus, stomach, duodenum, jejunum, colon), liver, or testis; or may be one of these tissues either in vivo or ex vivo. In practicing the method, the cell(s) giving rise to the cellular membrane may be transformed with the nucleic acid of Seq. I.D. Nos. 1 or 3 and maintained under conditions favoring functional expression of the transporter. A cell may be monitored for expression of the transporter by measuring the presence of calcium in the cell or transmembrane current flow. The invention also extends to a cell so transformed (e.g., a *Xenopus laevis* oocyte as described below).

In a fourth aspect, the invention comprises a method of identifying chemicals capable of interacting with the transporter, whether the protein is integral with a cellular membrane or present as a free species. Such chemicals may include antibodies or other targeting molecules that bind to the protein for purposes of identification, or which affect (e.g., by modulation or inhibition) the transport properties of the protein; and transportable species other than calcium.

In a fifth aspect, the invention comprises a method of blocking or inhibiting the uptake of calcium by cells having a calcium-transport protein in accordance herewith. In one embodiment, the method comprises the steps of causing an antibody or other targeting molecule to bind to the protein in a manner that inhibits calcium transport. In another embodiment, a nucleic acid complementary to at least a portion of the nucleic acid encoding the calcium-transport protein is introduced into the cells. The complementary nucleic acid blocks functional expression of the calcium-transport protein.

BRIEF DESCRIPTION OF THE DRAWINGS

The foregoing discussion will be understood more readily from the following detailed description of the invention, when taken in conjunction with the accompanying drawings, in which:

FIGS. 3A and 3B illustrate the primary peptide structure of a human calcium transporter corresponding to SEQ ID NO:2;

FIGS. 4A and 4B illustrate the primary peptide structure of a rat calcium transporter corresponding to SEQ ID NO:4;

FIGS. 5A–5E graphically illustrate various calcium-uptake properties of rat CaT1 proteins;

FIG. 7A depicts the response of *Xenopus laevis* oocytes expressing CaT1 to $Na^+$ in the absence of $Ca^{2+}$;

FIG. 7B depicts the response of *Xenopus laevis* oocytes expressing CaT1to $Ca^{2+}$ in the presence of $Na^+$ at low concentrations;

FIGS. 8A and 8B depict the charge-to-$^{45}Ca^{2+}$ ratio in voltage-clamped, CaT1-expressing oocytes in the presence of and in the absence of $Na^+$, respectively; and FIG. 9 depicts the response of voltage-clamped, CaT1-expressing oocytes to $Ca^{2+}$, $Ba^{2+}$, $Sr^{2+}$, and $Mg^{2+}$.

DETAILED DESCRIPTION OF THE PREFERRED EMBODIMENTS

1. CaT1 and its Nucleic Acids

With reference to Seq. I.D. No. 1, a human-derived cDNA having a nucleotide sequence encoding a calcium-transport protein contains 2218 nucleotides; an open reading frame of 2175 base pairs (bp) encodes a protein having 725 amino acids, which is set forth as Seq. ID. No. 2. With reference to Seq. I.D. No. 3, a rat-derived cDNA having a nucleotide sequence encoding a calcium-transport protein contains 2995 nucleotides; an open reading frame of 2181 base pairs (bp) encodes a protein having 727 amino acids, which is set forth as Seq. ID. No. 4. This protein is set forth as Seq. ID. No. 4. The designation CaT1 is herein used interchangeably to refer to the human protein of Seq. I.D. No. 2 and the rat protein of Seq. I.D. No. 4.

Figure 1:
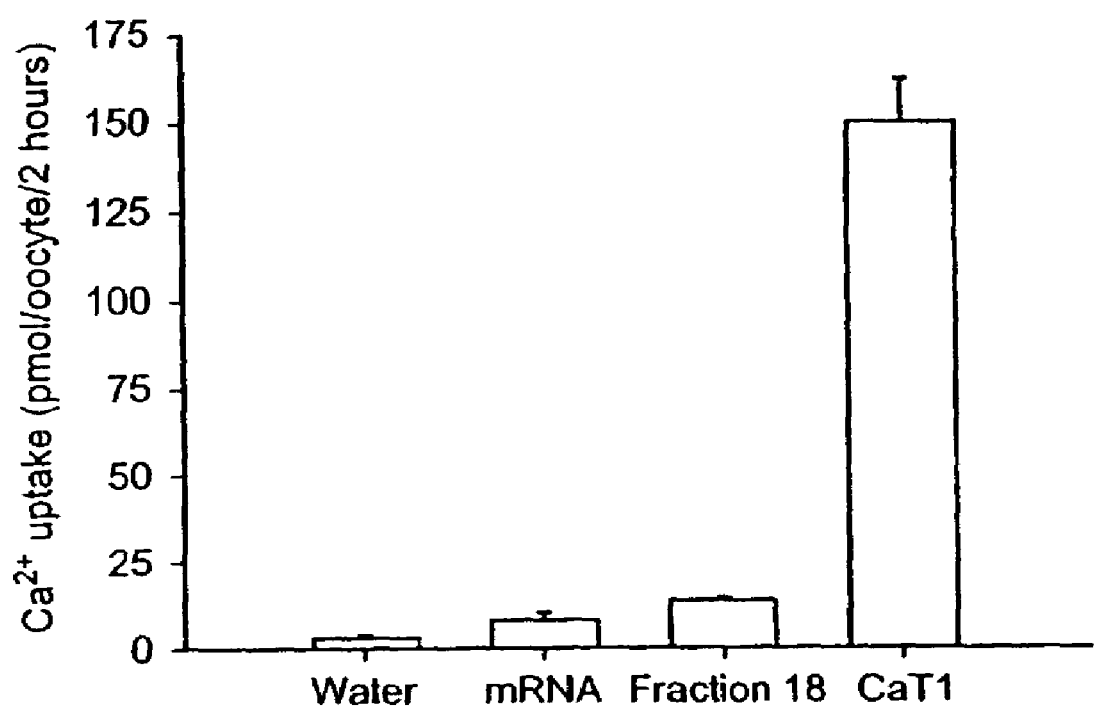
FIG. 1 graphically illustrates identification of CaT1 in *Xenopus laevis* oocytes by means of a calcium-uptake assay.
Figure 2A:
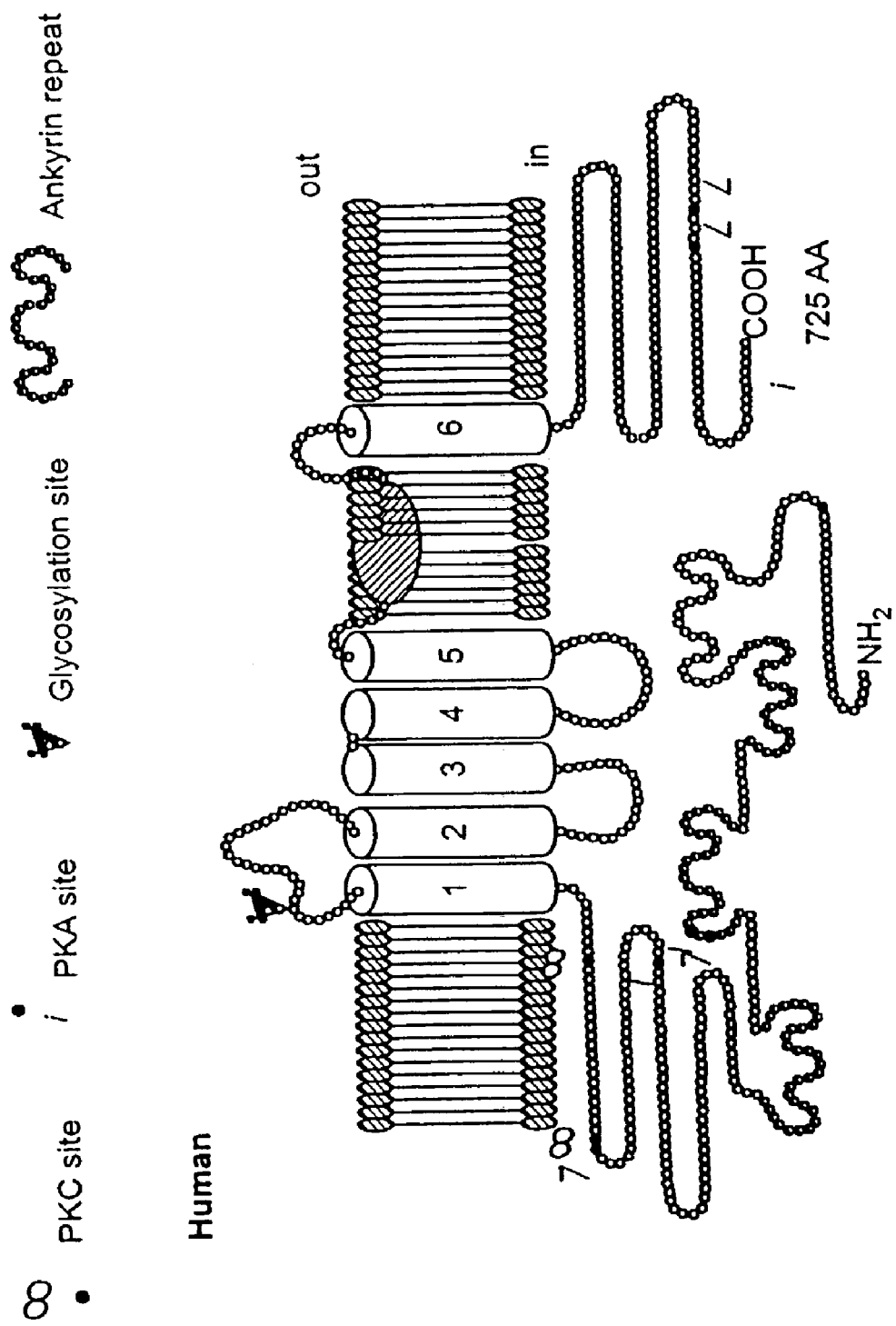
FIGS. 2A and 2B schematically illustrate the structure and topology of a human and a rat calcium transporter, respectively, in accordance herewith.
Figure 2B:
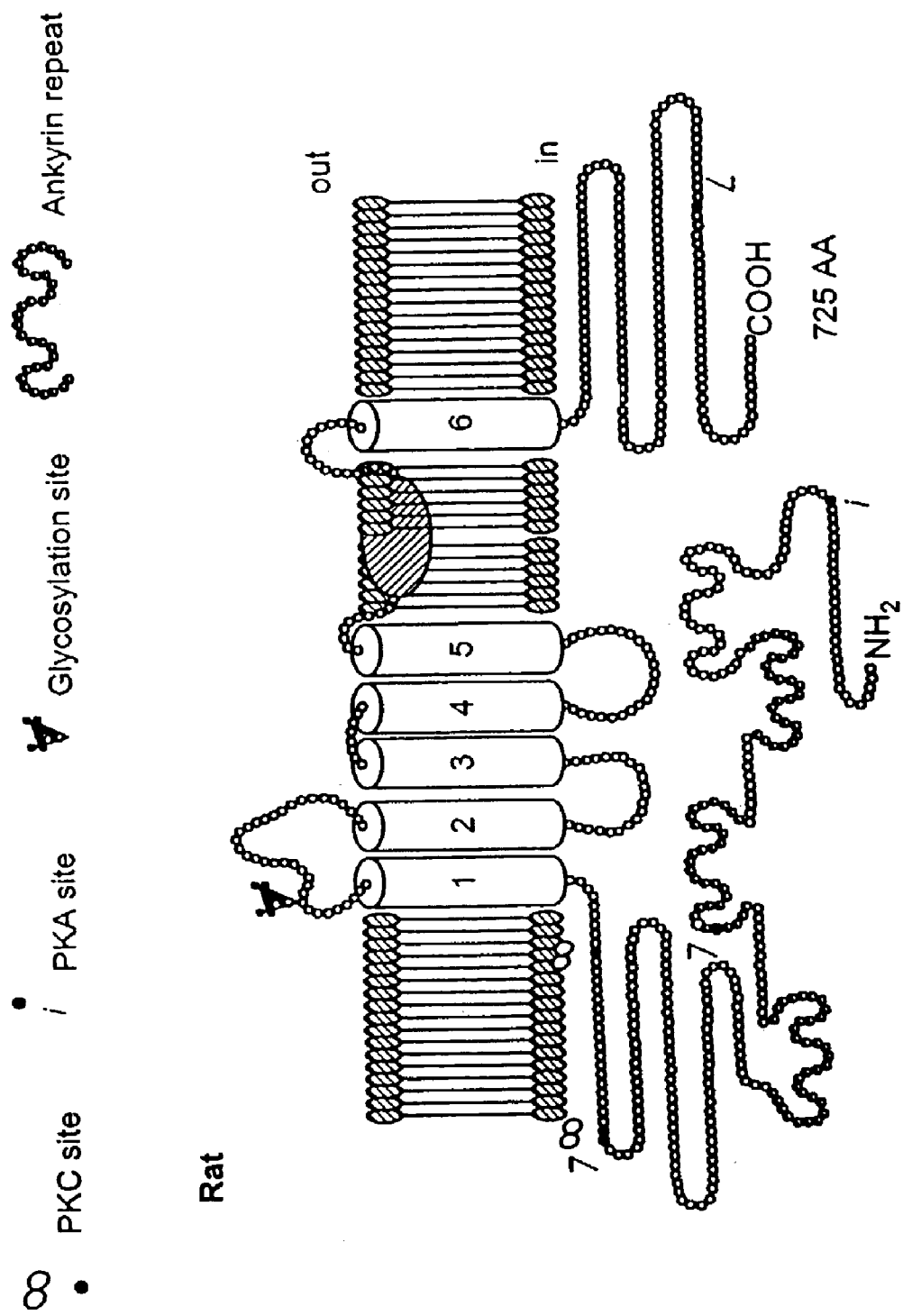

The predicted relative molecular mass of rat CaT1 is 83,245 ($M_r$=83.2 kDa), which is consistent with the molecular weight obtained by in vitro translation without microsomes (84 kDa). Hydropathy analysis suggests that the calcium transporter is a polytopic protein containing six transmembrane domains (TMs) with an additional short hydrophobic stretch between TM5 and 6 as illustrated in FIG. 1. Consistent with the molecular weight of the protein obtained by in vitro translation in the presence of microsomes (89 kDa), an N-glycosylation site is predicted in the first extracellular loop of the protein. The amino-terminal hydrophilic segment (326 amino acid residues) of rat CaT1 contains four ankyrin repeat domains, suggesting that the protein may somehow associate with the spectrin-based membrane cytoskeleton. The carboxyl terminus (150 amino-acid residues) contains no recognizable motifs. Putative phosphorylation sites for protein kinases A (PKA) and C (PKC) are present in the cytoplasmic domains, suggesting that transport activity could be regulated by phosphorylation. FIGS. 2 and 3 illustrate the primary structures of human and rat CaT1, respectively, showing the transmembrane domains as well as glycosylation, PKA, and PKC sites, and ankyrin repeat sequences.

The human protein shows 75% amino acid sequence identity to the recently cloned rabbit apical epithelial calcium channel ECaC (see Hoenderop et al., *J. Biol. Chem.* 296:8375–8378 (1999)) when using the BESTFIT sequence alignment program. There are, however, numerous differences between the proteins, in particular with respect to the amino- and carboxyl-terminal cytoplasmic domains, which are considerably more conserved between the rat and human CaT1 than between either transporter and ECaC; the number of ankyrin repeats; the number and distribution of PKA and PKC phosphorylation sites; and their N-glycosylation sites. In particular, the amino- and carboxyl-terminal cytoplasmic domains of CaT1 from rat and ECaC from rabbit exhibit a lower degree of similarity than the equivalent regions of rat CaT1 and partial sequences obtained from human small intestine (not shown) by homology screening using the CaT1 cDNA as a probe. Comparisons of sequences of 150 amino acids in the amino- or carboxyl-terminal cytoplasmic domains revealed 90% and 74% identities respectively, between rat and human CaT1 but only 61% and 50% identities, respectively, between CaT1 and ECaC. CaT1 has four ankyrin repeats and one PKA phosphorylation site in its amino-terminal segment, whereas ECaC contains three ankyrin repeats and no PKA site in the same region. In contrast, ECaC possesses three PKC sites and two PKA sites in its carboxyl-terminus, whereas CaT1 has only one PKC site and no PKA sites in the same region. In addition, CaT1 lacks the putative N-glycosylation site found in ECaC between the pore region and transmembrane domain 6. A striking difference between CaT1 and ECaC is that ECaC is abundant in the distal tubules and cortical collecting duct of rabbit kidney, while the CaT1 mRNA was undetectable in rat kidney, based on Northern analysis and in situ hybridization.

Additional homology searches of available protein databases revealed significant similarities between CaT1 and the capsaicin receptor, VR1 (see Caterina et al., *Nature* 389: 816–824 (1997)), and OSM-9, a *C. elegans* membrane protein involved in olfaction, mechanosensation and olfactory adaptation (see Colbert et al., *J. Neurosci.* 17:8259–8269 (1997)). These proteins are structurally related to the family of putative store-operated calcium channels, among which the first two identified were the *Drosophila* retinal proteins, TRP (see Montell et al., *Neuron* 2:1313–1323 (1989)) and TRPL (see Phillips et al., *Neuron* 8:631–642 (1992)). Based on the program BESTFIT, CaT1 shows 33.7% and 26.7% identities to VR1 and OSM-9, respectively, over a stretch of at least 500 residues, as well as 26.2% and 28.9% identities to TRP and TRPL, respectively, in more restricted regions (residues 552–593 for TRP and residues 556–593 for TRPL). The latter region covers part of the pore region and the last transmembrane domain. A common feature of all of these proteins is the presence of six TMs with a hydrophobic stretch between TM5 and TM6, resembling one of the four repeated motifs of 6 TMs in the voltage-gated channels. Another common feature is the presence of three to four ankyrin repeat domains in the cytoplasmic N-terminal region. Of note, members of the polycystin family also possess 6 transmembrane segments (30–32) and show a modest degree of homology to CaT1 in small regions of the predicted amino acid sequences (residues 596–687 in PKD2, 23% identity; and residues 381–483 in PKD2L, 26% identity), but the polycystins contain no ankyrin repeats. As explained below, however, it is unlikely that CaT1 is another subtype of capsaicin-gated or store-operated ion channels.

A homology search using the CaT1 sequence in expressed sequence tag (EST) databases revealed the following sequences with high degrees of similarity to CaT1 (names refer to GenBank accession numbers and % identities to nucleotide identities): AI101583 from rat brain (99%); AI007094 from mouse thymus (96%); AA447311, AA469437, AA579526 from human prostate (87%, 85%, 84%, respectively), W88570 from human fetal liver spleen (91%); AA078617 from human brain (85%); T92755 from human lung (92%).

2. Isolation and Analysis of CaT1

To clone the gene(s) encoding CaT1, an expression cloning strategy using *Xenopus laevis* oocytes as the expression system was employed. Functional screening of a rat duodenal library by measuring $^{45}Ca^{2+}$ uptake resulted in the isolation of a cDNA clone encoding CaT1. We found that oocytes injected with mRNA from rat duodenum or cecum exhibited reproducible increases in $Ca^{2+}$ uptake over water-injected control oocytes. After size-fractionation of rat duodenal poly(A)$^+$ RNA, we detected a substantial increase in $^{45}Ca^{2+}$ uptake by injection of RNA from a 2.5 to 3 kb pool (FIG. 1). A library was constructed using this RNA pool, and a single clone was isolated from this size-fractionated cDNA library by screening progressively smaller pools of clones for their ability to induce $^{45}Ca^{2+}$ uptake in cRNA-injected oocytes. The resultant 3-kb cDNA produced large increases in $Ca^{2+}$ uptake (~30 fold) when expressed in oocytes.

The experimental procedures we employed were as follows.

Expression Cloning—Expression cloning using *Xenopus* oocytes was performed in accordance with known techniques as described in Romero et al., *Methods Enzymol.* 296:17–52 (1998), hereby incorporated by reference. In particular, duodenal poly(A)$^+$ RNA from rats fed a calcium-deficient diet for 2 weeks was size-fractionated. A cDNA library was then constructed from the fractions of 2.5 to 3 kilobases (kb) that stimulated $^{45}Ca^{2+}$ uptake activity when expressed in oocytes. The RNAs synthesized in vitro from pools of ~500 clones were injected into oocytes, and the abilities of the pools to stimulate $Ca^{2+}$ uptake were assayed. A positive pool was sequentially subdivided and assayed in the same manner until a single clone was obtained. The cDNA clone was sequenced bidirectionally.

$^{45}Ca^{2+}$ uptake assay—Defolliculated *Xenopus laevis* oocytes were injected with either 50 nl of water or RNA. $^{45}Ca^{2+}$ uptake was assayed 3 days after injection of poly(A)$^+$ or 1–3 days a injection of synthetic complementary RNA (cRNA). For expression cloning, oocytes were incubated in modified Barth's solution supplemented with 1 mM $SrCl_2$ (to avoid excessive loading of oocytes with $Ca^{2+}$) as well as penicillin, streptomycin and gentamycin at 1 mg/ml. Standard uptake solution contained the following components (in mM): NaCl 100, KCl 2, $MgCl_2$ 1, $CaCl_2$ 1 (including $^{45}Ca^{2+}$), Hepes 10, pH 7.5. Uptake was performed at room temperature for 30 minutes (for the expression cloning procedure, 2 hour uptakes were employed), and oocytes were washed 6 times with ice-cold uptake medium plus 20 mM $MgCl_2$. The effects of capsaicin or L-type channel blockers on $Ca^{2+}$ uptake were studied in uptake solution by addition of 50 μM capsaicin (in ethanol solution, final concentration 0.05%) or 10–100 μM calcium channel blockers in water (nifedipine was diluted with uptake solution from 100 mM DMSO stock solution). Control experiments were performed with the appropriate ethanol and DMSO concentrations. Unless stated specifically, data are presented as means obtained from at least three experiments with 7 to 10 oocytes per group with standard error of the mean (S.E.M.) as the index of dispersion. Statistical significance was defined as having a P value of less than 0.05 as determined by Student's t-test.

In situ hybridization—Digoxigenin-labeled sense and antisense run-off transcripts were synthesized. CaT1 cRNA probes were transcribed from a PCR fragment that contains about 2.7 kb of CaT1 cDNA (nucleotides 126–2894) flanked at either end by promoter sequences for SP6 and T7 RNA polymerases. Sense and anti-sense transcripts were alkali-hydrolyzed to an average length of 200–400 nucleotides. In situ hybridization was performed on 10 µm cryosections of fresh-frozen rat tissues. Sections were immersed in slide mailers in hybridization solution composed of 50% formamide, 5×SSC, 2% blocking reagent, 0.02% SDS and 0.1% N-laurylsarcosine, and hybridized at 68° C. for 16 hours with sense or antisense probe at a concentration of about 200 ng/ml. Sections were then washed 3 times in 2×SSC and twice for 30 min in 0.2×SSC at 68° C. After washing, the hybridized probes were visualized by alkaline phosphatase histochemistry using alkaline-phosphatase-conjugated anti-digoxigenin Fab fragments and bromochloroindolyl phosphate/nitroblue tetrazolium (BCIP/NBT).

In vitro transcription was performed with the mMESSAGE mMACHINE T7 Kit (Ambion, Austin, Tex.). In vitro translation of the CaT1 protein was performed with the Rabbit Reticulocyte Lysate System (Promega, Madison, Wis.).

3. Tissue Distribution of CaT1

Northern analysis of rat tissues revealed a strong 3.0-kb band in rat small intestine and a weaker 6.5-kb band in brain, thymus and adrenal gland. No CaT1 transcripts were detected in heart, kidney, liver, lung, spleen and skeletal muscle. Northern analysis of the gastrointestinal tract revealed that the 3-kb CaT1 transcript is expressed in duodenum and proximal jejunum, cecum and colon but not in stomach, distal jejunum or ileum. The CaT1 mRNA in rat duodenum was not regulated by 1,25-dihydroxyvitamin $D_3$ nor by calcium deficiency in vivo.

In situ hybridization revealed expression of CaT1 mRNA in the absorptive epithelial cells of duodenum, proximal jejunum, cecum and colon but not in ileum. CaT1 mRNA is expressed at high levels in duodenum and cecum, at lower levels in proximal jejunum and at very low levels in colon. In all CaT1-expressing intestinal segments, mRNA levels were observed to be higher at the villi tips than in the villi crypts. No signals were detected in the kidney under the same experimental conditions or in sense controls.

Northern analysis procedures were as follows. Poly(A)$^+$ RNA (3 µg) from rat tissues were electrophoresed in formaldehyde-agarose gels and transferred to nitrocellulose membranes. The filters were probed with $^{32}P$-labeled full-length CaT1 cDNA, hybridized at 42° C. with a solution containing 50% formamide, 5×SSPE, 2× Denhardt's solution, 0.1% SDS and 100 µg/ml denatured salmon sperm DNA (and washed with 5×SSC/0.1% SDS at 50° C. for 2×30 minutes and 0.1×SSC at 65° C. for 3×30 minutes. Autoradiography was performed at −80° C. for 1 to 2 days.

4. Characterization of Functional Properties of CaT1 by $^{45}Ca^{2+}$ Uptake Assay Since CaT1 shares some similarity in its structure with the capsaicin receptor (VR1), TRP and TRPL channels, we tested the possibility that the activity of CaT1 could be stimulated by capsaicin or calcium-store depletion using the uptake assay described above. Capsaicin (up to 50 µM) did not stimulate CaT1-mediated $^{45}Ca^{2+}$ uptake in oocytes. Instead of stimulating $Ca^{2+}$ entry, depletion of calcium stores by thapsigargin treatment decreased CaT1-mediated $Ca^{2+}$ activity to about 20% of its baseline activity (FIG. 5A). Based on these data, it is unlikely that CaT1 is another subtype of capsaicin-gated or store-operated ion channels.

Figure 5E:
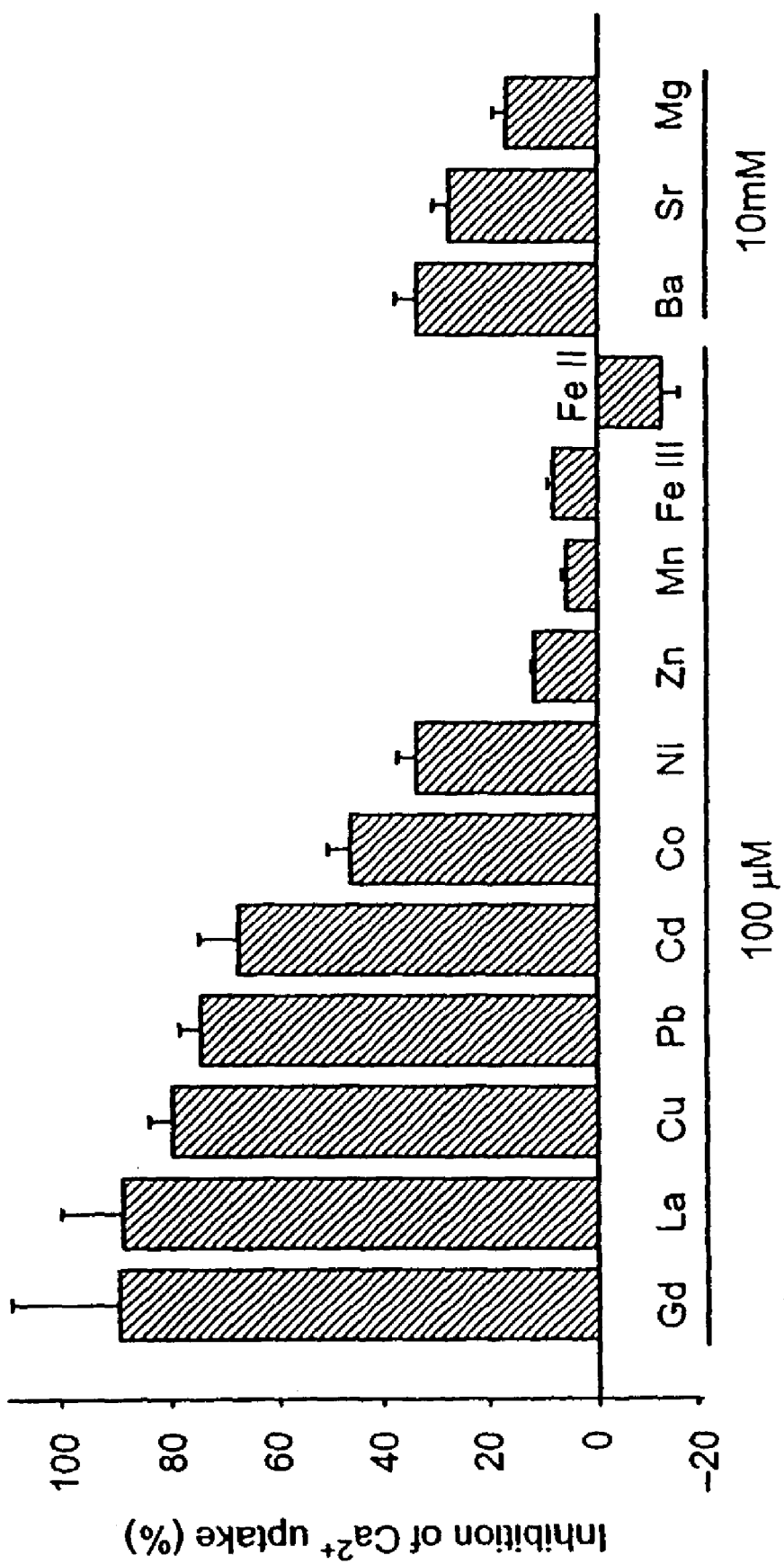

When expressed in oocytes, CaT1-mediated $^{45}Ca^{2+}$ uptake was linear for up to 2 hours. $Ca^{2+}$ uptake was concentration-dependent and saturable, with an apparent Michaelis constant ($K_m$) of 0.44±0.07 mM (FIG. 5B). This $K_m$ is appropriate for absorbing $Ca^{2+}$ from the intestine, which is normally around 1 to 5 mM after a calcium-containing meal, and accords with values reported in physiological studies of calcium absorption in rat, hamster, pig, and human intestines. Consistent with the prediction from early studies that apical $Ca^{2+}$ uptake is not energy-dependent, CaT1-mediated transport did not appear to be coupled to $Na^+$, $Cl^-$ or $H^+$ (FIGS. 5C and 5D). To study the substrate specificity of CaT1, we initially performed inhibition studies of $^{45}Ca^{2+}$ uptake (1 mM $Ca^{2+}$) by various di- and trivalent cations (100 µM) (FIG. 5E). $Gd^{3+}$, $La^{3+}$, $Cu^{2+}$, $Pb^{2+}$, $Cd^{2+}$, $Co^{2+}$ and $Ni^{2+}$ produced marked to moderate inhibition, whereas $Fe^{2+}$, $Fe^{2+}$, $Mn^{2+}$ and $Ni^{2+}$ had no significant effects. In contrast, $Ba^{2+}$ and $Sr^{2+}$ had only slight inhibitory effects, even at a concentration of 10 mM, whereas $Mg^{2+}$ (10 mM) produced no significant inhibition (FIG. 5E).

$Ca^{2+}$ entry into enterocytes has, in general, been reported to be insensitive to classic voltage-dependent calcium channel blockers, and to be only slightly inhibited by verapamil. Among the three classes of L-type calcium channel blockers that we tested—nifedipine, diltiazem and verapamil—only the latter two modestly inhibited CaT1-mediated $Ca^{2+}$ uptake (by 10–15%) at relatively high concentrations (10–100 µM).

5. Electrophysiological Properties of CaT1—Mediated Transport

Two-microelectrode voltage clamp experiments were performed using standard techniques (see Chen et al., *J. Biol. Chem.* 274:2773–2779 (1999)) using a commercial amplifier and pCLAMP software (Version 7, Axon Instruments, Inc., Foster City, Calif.). An oocyte was introduced into the chamber containing $Ca^{2+}$-free solution and was incubated for about 3 minutes before being clamped at −50 mV and subjected to measurements. In experiments involving voltage ramps or jumps, whole-cell current and voltage were recorded by digitizing at 300 µs/sample and by Bessel filtering at 10 kHz. When recording currents at a holding potential, digitization at 0.2 s/sample and filtering at 20 Hz were employed. Voltage ramping consisted of pre-holding at −150 mV for 200 ms to eliminate capacitive currents and a subsequent linear increase from −150 to +50 mV, with a total duration of 1.4. Voltage jumping consisted of 150 ms voltage pulses of between −140 and +60 mV, in increments of +20 mV. Steady-state currents were obtained as the average values in the interval from 135 to 145 ms after the initiation of the voltage pulses. For experiments involving voltage-clamped $^{45}Ca^{2+}$ uptake, $Ca^{2+}$-evoked currents and uptake of $^{45}Ca^{2+}$ were simultaneously measured at −50 mV, using a method similar to that described in Chen et al. (cited above).

It is found that CaT1-mediated $Ca^{2+}$ transport is driven by the electrochemical gradient of $Ca^{2+}$. There is no evidence for coupling of $Ca^{2+}$ uptake to other ions or to metabolic energy. While CaT1-mediated $Ca^{2+}$ transport is electrogenic and voltage dependent, its kinetic behavior is distinct from that of the voltage-dependent calcium channels, which are operated by membrane voltage. At a macroscopic level, the kinetic properties of CaT1 resemble those of a facilitated transporter, and patch clamp studies have not as yet provided any evidence for distinct single-channel activity. CaT1 may represent an evolutionary transition between a channel and a facilitated transporter.

Figure 6A:
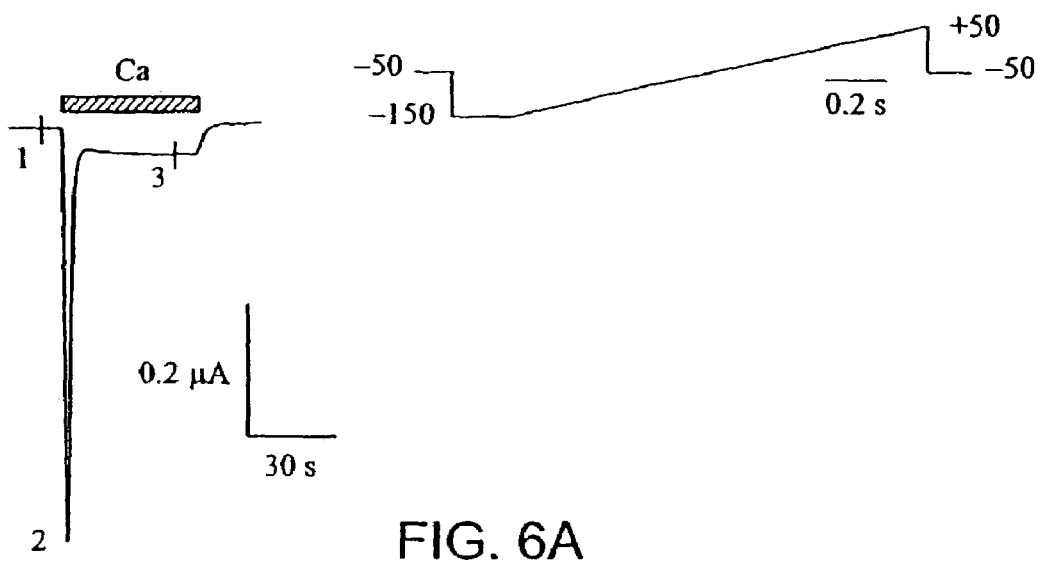
FIG. 6A and 6B depict responses of *Xenopus laevis* oocytes expressing CaT1 following external application of $Ca^{2+}$.
Figure 6B:
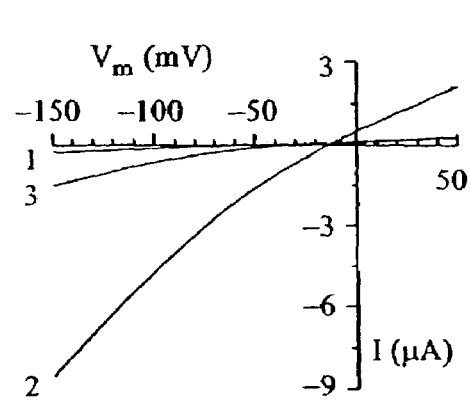
Figure 6C:
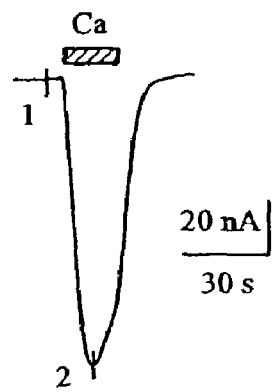
FIG. 6C and 6D depict responses of *Xenopus laevis* oocytes expressing CaT1following injection of the calcium chelator EGTA (i.e., ethylene glycol-bis(β-aminoethyl-ether)-N,N,N',N'-tetraacetic acid)
Figure 6D:
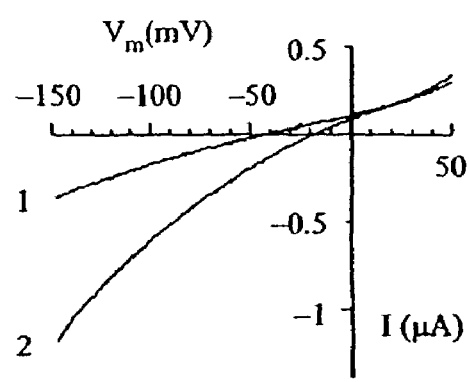

More specifically, external application of $Ca^{2+}$ to oocytes expressing CaT1 generated inward currents at a holding potential of −50 mV (FIG. 6A), which were absent in control oocytes. Addition of 5 mM $Ca^{2+}$ evoked an overshoot of inward current to several hundred nA followed by a rapid reduction to a plateau value of 20–50 nA (FIG. 6A). CaT1- mediated current was also voltage-dependent, as revealed by current-voltage (I-V) curves (FIG. 6B). The peak current is due to endogenous $Ca^{2+}$-activated chloride-channel currents because it could be blocked by chloride channel blockers such as flufenamate. The plateau also contained flufenamate-inhibitable currents, suggesting that some endogenous, $Ca^{2+}$-activated chloride channels remained active during this phase. Chelating intracellular $Ca^{2+}$ by injection of EGTA into oocytes expressing CaT1 to a final concentration of 1–2 mM resulted in a three- to five-fold increase in $Ca^{2+}$ uptake and abolished the overshoot of the current (FIG. 6A). Under the same condition, EGTA-injected control oocytes produced no detectable currents. Therefore, CaT1 likely mediates the observed $Ca^{2+}$-evoked currents in EGTA-injected oocytes (FIGS. 6C, 6D).

In the absence of $Ca^{2+}$, oocytes expressing CaT1 exhibited a significant permeability to $Na^+$ at hyperpolarized potentials (FIG. 7A). Similar conductances were observed for $K^+$, $Rb^+$ and $Li^+$ ($K^+ \approx Rb^+ > Na^+ > Li^+$). CaT1-mediated permeation of monovalent cations exhibited inward rectification because the sum of endogenous $K^+$ and $Na^+$ concentrations is high in *Xenopus* oocytes. In addition, $Ca^{2+}$-evoked currents were slightly lower in the presence of 100 mM $Na^+$ than in its absence (FIG. 7B), presumably due to the presence of modest competition between $Ca^{2+}$ and $Na^+$ for permeation via CaT1. With prolonged application of $Ca^{2+}$ (30 minutes) to non-clamped oocytes expressing CaT1, $Ca^{2+}$ entry was enhanced by extracellular $Na^+$ (FIG. 5C).

In order to determine whether $Ca^{2+}$ entry via CaT1 is associated with influx or efflux of other ions, the charge-to-$^{45}Ca^{2+}$ influx ratio was determined in voltage clamped oocytes pre-injected with EGTA (FIG. 8A). In the absence of external $Na^+$, the calculated ratio was not significantly different (FIG. 8B), indicating that permeation of $Ca^{2+}$ alone accounts for the observed inward currents. The findings that EGTA injection increases CaT1 activity and that the calcium-evoked current decays upon prolonged calcium application (FIG. 8A) suggest that CaT1 is controlled by a feedback regulatory mechanism, possibly through interaction of intracellular calcium with the transporter.

CaT1 is relatively specific for $Ca^{2+}$, showing only moderate ability to transport other ions. Despite their weak inhibitory potencies, $Ba^{2+}$ and $Sr^{2+}$, but not $Mg^{2+}$, evoked CaT1-specific currents albeit with much smaller amplitudes (FIG. 9). In EGTA-injected oocytes expressing CaT1 that were clamped at –50 mV, currents due to addition of 5 mM $Ba^{2+}$ and $Sr^{2+}$ represented 12±2% and 20±4% (n=17), respectively, of the current evoked by 5 mM $Ca^{2+}$. No significant $Sr^{2+}$-evoked or $Ba^{2+}$-evoked currents were observed in control oocytes under similar conditions. Other divalent metal ions, including $Fe^{2+}$, $Mn^{2+}$, $Zn^{2+}$, $Co^{2+}$, $Ni^{2+}$, $Cu^{2+}$, $Pb^{2+}$ and $Cd^{2+}$, and the trivalent metal ions $Fe^{3+}$, $La^{3+}$ and $Gd^{3+}$ (each at 100 µM), did not evoke measurable currents when applied to oocytes expressing CaT1. In agreement with their inhibitory effects on $^{45}Ca^{2+}$ uptake (see FIG. 4E), $Gd^{3+}$, $La^{3+}$, $Cu^{2+}$, $Pb^{2+}$, $Cd^{2+}$, $Co^{2+}$ and $Ni^{2+}$ (each at 100 µM) all inhibited the $Ca^{2+}$-evoked currents, whereas the same concentration of $Fe^{3+}$, $Mn^{2+}$ and $Zn^{2+}$ had no observable effects. Magnesium is neither a substrate (up to 20 mM) nor an effective blocker of CaT1.

Patch-clamp methodology was employed to search for single-channel activities using cell-attached and excised membrane patches. Patch pipettes were prepared from 7052 Corning glass capillaries. The pipette tip resistance was 5–10 MΩ. Seal resistances of >10 GΩ were employed in single channel experiments, and currents were measured using an integrating patch-clamp amplifier with filtering at 3 kHz through an 8-pole Bessel filter. In cell-attached patches, the resting potential corresponded to holding the patches at 0 mV. For data acquisition and analysis, voltage stimuli were applied and single channel currents digitized (50–200 us per point) and analyzed using a PC, a Digidata Pack and programs based on pCLAMP 6.

No CaT1-specific channel activities could be identified that were clearly distinguishable from the endogenous channels present in control oocytes, based on studies of 52 patches from 46 oocytes (EGTA- or non-EGTA-injected) obtained from seven frogs.

6. Applications of CaT1 and its Nucleic Acids

Although the full potential of CaT1 as a therapeutic target has not been investigated, the tissue distribution described above indicates several worthwhile treatment applications involving activation or inhibition of the CaT1 protein. Inhibition of CaT1, for example, may be used to treat kidney stones and various hypercalcemia conditions by restricting intestinal uptake of calcium. Stimulation of intestinal calcium uptake, on the other hand, could be used to treat conditions (such as osteoporosis and osteomalacia) characterized by reduced intestinal calcium absorption or reduced bone mass, as well as skin diseases (by stimulation of differentiation) and, possibly, hair growth. Given the potential role of calcium transport in various malignancies, modulation of CaT1 may prove useful in combating tumors.

CaT1 may be inhibited by pharmacological antagonists, blocking antibodies or by reducing transcription of its gene. Conversely, CaT1 may be stimulated by pharmacological agonists, stimulatory antibodies or by increasing transcription of its gene. Blocking or stimulatory antibodies against CaT1 are obtained in accordance with well-known immunological techniques, and a polyclonal mixture of such antibodies is screened for clones that exert an inhibitory or stimulatory effect on CaT1. The effect of pharmacological compounds or antibodies can be measured (and the efficacy of the treatment agent assayed) by observing the free cystolic calcium concentration (e.g., using a calcium-sensitive intracellular dye), activation of any calcium-sensitive intracellular processes (e.g., the activities of enzymes, gene expression, ion channels, the activity of other calcium-regulated transporters, or electrophysiological measurements (as described above)), or $^{45}Ca$-uptake studies (also as described above). The monoclonal antibody lines are then employed therapeutically in accordance with known inhibitory treatment methodologies. Alternatively, nucleic acid isolated or synthesized for complementarity to the sequences described herein can be used as anti-sense genes to prevent the expression of CaT1. For example, complementary DNA may be loaded into a suitable carrier such as a liposome for introduction into a cell. A nucleic acid having 8 or more nucleotides is capable of binding to genomic nucleic acid or mRNA. Preferably, the anti-sense nucleic acid comprises 30 or more nucleotides to provide necessary stability to a hybridization product with genomic DNA or mRNA.

Nucleic acid synthesized in accordance with the sequences described herein also have utility to generate CaT1 polypeptides or portions thereof. Nucleic acid exemplified by Seq. I.D. Nos. 1 or 3 can be cloned in suitable vectors or used to isolate nucleic acid. The isolated nucleic acid is combined with suitable DNA linkers and promoters, and cloned in a suitable vector. The vector can be used to transform a host organism such as *E. coli* and to express the encoded polypeptide for isolation.

Although the present invention has been described with reference to specific details, it is not intended that such details should be regarded as limitations upon the scope of the invention, except as and to the extent that they are included in the accompanying claims.

What is claimed is:

1. A method for modulating transmembrane calcium transport, the method comprising the steps of:
   a. providing a cell that expresses a nucleic acid encoding a protein that transports calcium across a membrane, the nucleic acid comprising the nucleotide sequence of SEQ ID NO; 1, or substitutions or modifications thereof, wherein the substituted or modified nucleic acid sequence encodes a protein that transports calcium across a cellular membrane wherein said protein is at least 75% identical to SEQ ID NO:2 but distinct from ECaC; and
   b. contacting the cell with a chemical that interacts with the protein so as to affect its calcium transmembrane transporting activity, thereby altering a rate of calcium transport across the membrane.

2. The method of claim 1, wherein the chemical is an antibody.

3. The method of claim 1, wherein the chemical is a nucleic acid.

4. The method of claim 1, wherein the chemical is an inhibitor.

5. The method of claim 1, wherein the cell is an epithelial cell.

6. The method of claim 1, wherein the cell is a *Xenopus laevis* oocyte, placenta cell, pancreas cell, prostate cell, kidney cell, gastrointestinal tract cell, liver cell, hair follicle cell, testis cell, or cancer cell.

7. The method of claim 6, wherein the cell is an esophageal cell, stomach cell, duodenum cell, jejunum cell, or colon cell.

8. The method of claim 6, wherein the cell is the chronic myelogenous leukemia cell line K-562, the colorectal adenocarcinoma cell line SW480, a bone cell, a leukemia cell, a prostate cancer cell, a breast cancer cell, a esophagus cancer cell, a stomach cancer cell, or a colon cancer cell.

9. The method of claim 1, wherein the chemical alters the calcium transport properties of the protein.

10. The method of claim 1, wherein the chemical binds to the protein.

11. The method of claim 1, wherein the protein is integral with the cellular membrane.

12. The method of claim 1, wherein the chemical is present as a free species.

13. A method of identifying the ability of a chemical to alter transmembrane calcium transport, the method comprising the steps of:
   a. providing a cell that expresses a nucleic acid encoding a protein that transports calcium across a membrane, the nucleic acid comprising the nucleotide sequence of SEQ ID NO:1, or substitutions or modifications thereof, wherein the substituted or modified nucleic acid sequence encodes a protein that transports calcium across a cellular membrane wherein said protein is at least 75% identical to SEQ ID NO:2 but distinct from ECaC, the cell expressing the protein in a membrane of the cell;
   b. contacting the membrane with at least one candidate antibody or nucleic acid;
   c. measuring the transmembrane calcium transport rate via the protein in the presence of the chemical; and
   d. comparing the measurement of step (c) with the transmembrane calcium transport rate via the protein in the absence of the chemical, wherein the comparison indicates whether the chemical has altered the transmembrane calcium transport.

14. The method of claim 13, wherein the cell is an epithelial cell.

15. The method of claim 13, wherein the cell is a *Xenopus laevis* oocyte, placenta cell, pancreas cell, prostate cell, kidney cell, gastrointestinal tract cell, liver cell, hair follicle cell, testis cell, or cancer cell.

16. The method of claim 15, wherein the cell is an esophageal cell, stomach cell, duodenum cell, jejunum cell, or colon cell.

17. The method of claim 15, wherein the cell is the chronic myelogenous leukemia cell line K-562, the colorectal adenocarcinoma cell line SW480, a bone cell, a leukemia cell, a prostate cancer cell, a breast cancer cell, an esophagus cancer cell, a stomach cancer cell, and a colon cancer cell.

18. The method of claim 13, wherein the chemical alters the transport properties of the protein.

19. The method of claim 13, wherein the chemical binds to the protein.

20. The method of claim 13, wherein the protein is integral with the cellular membrane.

21. The method of claim 13, wherein the chemical is present as a free species.

* * * * *

```
                              SEQUENCE LISTING

<160> NUMBER OF SEQ ID NOS: 4

<210> SEQ ID NO 1
<211> LENGTH: 2218
<212> TYPE: DNA
<213> ORGANISM: Homo sapiens
<220> FEATURE:
<221> NAME/KEY: CDS
<222> LOCATION: (41)..(2218)

<400> SEQUENCE: 1
cctcggcctc aggcccccaa ggtagccggc cctacacccc atg ggt ttg tca ctg          55
                                             Met Gly Leu Ser Leu
                                              1               5 ccc aag gag aaa ggg cta att ctc tgc cta tgg agc aag ttc tgc aga         103
Pro Lys Glu Lys Gly Leu Ile Leu Cys Leu Trp Ser Lys Phe Cys Arg
                 10                  15                  20 tgg ttc cag aga cgg gag tcc tgg gcc cag agc cga gat gag cag gac         151
Trp Phe Gln Arg Arg Glu Ser Trp Ala Gln Ser Arg Asp Glu Gln Asp
             25                  30                  35 ctg ctg cag cag aag agg atc tgg gag tct cct ctc ctt cta gct gcc         199
Leu Leu Gln Gln Lys Arg Ile Trp Glu Ser Pro Leu Leu Leu Ala Ala
         40                  45                  50 aaa gat aat gat gtc cag gcc ctg aac aag ttg ctc aag tat gag gat         247
Lys Asp Asn Asp Val Gln Ala Leu Asn Lys Leu Leu Lys Tyr Glu Asp
     55                  60                  65 tgc aag gtg cac cat aga gga gcc atg ggg gaa aca gcg cta cac ata         295
Cys Lys Val His His Arg Gly Ala Met Gly Glu Thr Ala Leu His Ile
 70                  75                  80                  85 gca gcc ctc tat gac aac ctg gag gcc gcc atg gtg ctg atg gag gct         343
Ala Ala Leu Tyr Asp Asn Leu Glu Ala Ala Met Val Leu Met Glu Ala
                 90                  95                 100 gcc ccg gag ctg gtc ttt gag ccc atg aca tct gag ctc tat gag ggt         391
Ala Pro Glu Leu Val Phe Glu Pro Met Thr Ser Glu Leu Tyr Glu Gly
            105                 110                 115 cag act gca ctg cac atc gct gtt gtg aac cag aac atg aac ctg gtg         439
Gln Thr Ala Leu His Ile Ala Val Val Asn Gln Asn Met Asn Leu Val
        120                 125                 130 cga gcc ctg ctt gcc cgc agg gcc agt gtc tct gcc aga gcc aca ggc         487
Arg Ala Leu Leu Ala Arg Arg Ala Ser Val Ser Ala Arg Ala Thr Gly
    135                 140                 145 act gcc ttc cgc cgt agt ccc tgc aac ctc atc tac ttt ggg gag cac         535
Thr Ala Phe Arg Arg Ser Pro Cys Asn Leu Ile Tyr Phe Gly Glu His
150                 155                 160                 165 cct ttg tcc ttt gct gcc tgt gtg aac agt gag gag atc gtg cgg ctg         583
Pro Leu Ser Phe Ala Ala Cys Val Asn Ser Glu Glu Ile Val Arg Leu
                170                 175                 180 ctc att gag cat gga gct gac atc cgg gcc cag gac tcc ctg gga aac         631
Leu Ile Glu His Gly Ala Asp Ile Arg Ala Gln Asp Ser Leu Gly Asn
            185                 190                 195 aca gtg tta cac atc ctc atc ctc cag ccc aac aaa acc ttt gcc tgc         679
Thr Val Leu His Ile Leu Ile Leu Gln Pro Asn Lys Thr Phe Ala Cys
        200                 205                 210 cag atg tac aac ctg ttg ctg tcc tac gac aga cat ggg gac cac ctg         727
Gln Met Tyr Asn Leu Leu Leu Ser Tyr Asp Arg His Gly Asp His Leu
    215                 220                 225
```

-continued

| | | |
|---|---|---|
| cag ccc ctg gac ctc gtg ccc aat cac cag ggt ctc acc cct ttc aag<br>Gln Pro Leu Asp Leu Val Pro Asn His Gln Gly Leu Thr Pro Phe Lys<br>230                        235                  240                   245 | 775 |
| ctg gct gga gtg gag ggt aac act gtg atg ttt cag cac ctg atg cag<br>Leu Ala Gly Val Glu Gly Asn Thr Val Met Phe Gln His Leu Met Gln<br>                  250                  255                  260 | 823 |
| aag cgg aag cac acc cag tgg acg tat gga cca ctg acc tcg act ctc<br>Lys Arg Lys His Thr Gln Trp Thr Tyr Gly Pro Leu Thr Ser Thr Leu<br>265                        270                  275 | 871 |
| tat gac ctc aca gag atc gac tcc tca ggg gat gag cag tcc ctg ctg<br>Tyr Asp Leu Thr Glu Ile Asp Ser Ser Gly Asp Glu Gln Ser Leu Leu<br>280                        285                  290 | 919 |
| gaa ctt atc atc acc acc aag aag cgg gag gct cgc cag atc ctg gac<br>Glu Leu Ile Ile Thr Thr Lys Lys Arg Glu Ala Arg Gln Ile Leu Asp<br>295                        300                  305 | 967 |
| cag acg ccg gtg aag gag ctg gtg agc ctc aag tgg aag cgg tac ggg<br>Gln Thr Pro Val Lys Glu Leu Val Ser Leu Lys Trp Lys Arg Tyr Gly<br>310                        315                  320                  325 | 1015 |
| cgg ccg tac ttc tgc atg ctg ggt gcc ata tat ctg ctg tac atc atc<br>Arg Pro Tyr Phe Cys Met Leu Gly Ala Ile Tyr Leu Leu Tyr Ile Ile<br>                  330                  335                  340 | 1063 |
| tgc ttc acc atg tgc tgc atc tac cgc ccc ctc aag ccc agg acc aat<br>Cys Phe Thr Met Cys Cys Ile Tyr Arg Pro Leu Lys Pro Arg Thr Asn<br>                  345                  350                  355 | 1111 |
| aac cgc acg agc ccc cgg gac aac acc ctc tta cag cag aag cta ctt<br>Asn Arg Thr Ser Pro Arg Asp Asn Thr Leu Leu Gln Gln Lys Leu Leu<br>                  360                  365                  370 | 1159 |
| cag gaa gcc tac atg acc cct aag gac gat atc cgg ctg gtc ggg gag<br>Gln Glu Ala Tyr Met Thr Pro Lys Asp Asp Ile Arg Leu Val Gly Glu<br>375                        380                  385 | 1207 |
| ctg gtg act gtc att ggg gct atc atc atc ctg ctg gta gag gtt cca<br>Leu Val Thr Val Ile Gly Ala Ile Ile Ile Leu Leu Val Glu Val Pro<br>390                        395                  400                  405 | 1255 |
| gac atc ttc aga atg ggg gtc act cgc ttc ttt gga cag acc atc ctt<br>Asp Ile Phe Arg Met Gly Val Thr Arg Phe Phe Gly Gln Thr Ile Leu<br>                  410                  415                  420 | 1303 |
| ggg ggc cca ttc cat gtc ctc atc atc acc tat gcc ttc atg gtg ctg<br>Gly Gly Pro Phe His Val Leu Ile Ile Thr Tyr Ala Phe Met Val Leu<br>                  425                  430                  435 | 1351 |
| gtg acc atg gtg atg cgg ctc atc agt gcc agc ggg gag gtg gta ccc<br>Val Thr Met Val Met Arg Leu Ile Ser Ala Ser Gly Glu Val Val Pro<br>                  440                  445                  450 | 1399 |
| atg tcc ttt gca ctc gtg ctg ggc tgg tgc aat gtc atg tac ttc gcc<br>Met Ser Phe Ala Leu Val Leu Gly Trp Cys Asn Val Met Tyr Phe Ala<br>455                        460                  465 | 1447 |
| cga gga ttc cag atg cta ggc ccc ttc acc atc atg att cag aag atg<br>Arg Gly Phe Gln Met Leu Gly Pro Phe Thr Ile Met Ile Gln Lys Met<br>470                        475                  480                  485 | 1495 |
| att ttt ggc gac ctg atg cga ttc tgc tgg ctg atg gct gtg gtc atc<br>Ile Phe Gly Asp Leu Met Arg Phe Cys Trp Leu Met Ala Val Val Ile<br>                  490                  495                  500 | 1543 |
| ctg ggc ttt gct tca gcc ttc tat atc atc ttc cag aca gag gac ccc<br>Leu Gly Phe Ala Ser Ala Phe Tyr Ile Ile Phe Gln Thr Glu Asp Pro<br>                  505                  510                  515 | 1591 |
| gag gag cta ggc cac ttc tac gac tac ccc atg gcc ctg ttc agc acc<br>Glu Glu Leu Gly His Phe Tyr Asp Tyr Pro Met Ala Leu Phe Ser Thr<br>                  520                  525                  530 | 1639 |
| ttc gag ctg ttc ctt acc atc atc gat ggc cca gcc aac tac aac gtg<br>Phe Glu Leu Phe Leu Thr Ile Ile Asp Gly Pro Ala Asn Tyr Asn Val<br>535                        540                  545 | 1687 |

-continued

```
gac ctg ccc ttc atg tac agc atc acc tat gct gcc ttt gcc atc atc      1735
Asp Leu Pro Phe Met Tyr Ser Ile Thr Tyr Ala Ala Phe Ala Ile Ile
550                 555                 560                 565 gcc aca ctg ctc atg ctc aac ctc ctc att gcc atg atg ggc gac act      1783
Ala Thr Leu Leu Met Leu Asn Leu Leu Ile Ala Met Met Gly Asp Thr
            570                 575                 580 cac tgg cga gtg gcc cat gag cgg gat gag ctg tgg agg gcc cag att      1831
His Trp Arg Val Ala His Glu Arg Asp Glu Leu Trp Arg Ala Gln Ile
585                 590                 595 gtg gcc acc acg gtg atg ctg gag cgg aag ctg cct cgc tgc ctg tgg      1879
Val Ala Thr Thr Val Met Leu Glu Arg Lys Leu Pro Arg Cys Leu Trp
        600                 605                 610 cct cgc tcc ggg atc tgc gga cgg gag tat ggc ctg gga gac cgc tgg      1927
Pro Arg Ser Gly Ile Cys Gly Arg Glu Tyr Gly Leu Gly Asp Arg Trp
    615                 620                 625 ttc ctg cgg gtg gaa gac agg caa gat ctc aac cgg cag cgg atc caa      1975
Phe Leu Arg Val Glu Asp Arg Gln Asp Leu Asn Arg Gln Arg Ile Gln
630                 635                 640                 645 cgc tac gca cag gcc ttc cac acc cgg ggc tct gag gat ttg gac aaa      2023
Arg Tyr Ala Gln Ala Phe His Thr Arg Gly Ser Glu Asp Leu Asp Lys
            650                 655                 660 gac tca gtg gaa aaa cta gag ctg ggc tgt ccc ttc agc ccc cac ctg      2071
Asp Ser Val Glu Lys Leu Glu Leu Gly Cys Pro Phe Ser Pro His Leu
        665                 670                 675 tcc ctt cct atg ccc tca gtg tct cga agt acc tcc cgc agc agt gcc      2119
Ser Leu Pro Met Pro Ser Val Ser Arg Ser Thr Ser Arg Ser Ser Ala
    680                 685                 690 aac tgg gaa agg ctt cgg caa ggg acc ctg agg aga gac ctg cgt ggg      2167
Asn Trp Glu Arg Leu Arg Gln Gly Thr Leu Arg Arg Asp Leu Arg Gly
695                 700                 705 ata atc aac agg ggt ctg gag gac ggg gag agc tgg gaa tat cag atc      2215
Ile Ile Asn Arg Gly Leu Glu Asp Gly Glu Ser Trp Glu Tyr Gln Ile
710                 715                 720                 725 tga                                                                   2218
```

```
<210> SEQ ID NO 2
<211> LENGTH: 725
<212> TYPE: PRT
<213> ORGANISM: Homo sapiens

<400> SEQUENCE: 2

Met Gly Leu Ser Leu Pro Lys Glu Lys Gly Leu Ile Leu Cys Leu Trp
1               5                   10                  15

Ser Lys Phe Cys Arg Trp Phe Gln Arg Glu Ser Trp Ala Gln Ser
            20                  25                  30

Arg Asp Glu Gln Asp Leu Leu Gln Lys Arg Ile Trp Glu Ser Pro
        35                  40                  45

Leu Leu Leu Ala Ala Lys Asp Asn Asp Val Gln Ala Leu Asn Lys Leu
50                  55                  60

Leu Lys Tyr Glu Asp Cys Lys Val His His Arg Gly Ala Met Gly Glu
65                  70                  75                  80

Thr Ala Leu His Ile Ala Ala Leu Tyr Asp Asn Leu Glu Ala Ala Met
            85                  90                  95

Val Leu Met Glu Ala Ala Pro Glu Leu Val Phe Glu Pro Met Thr Ser
        100                 105                 110

Glu Leu Tyr Glu Gly Gln Thr Ala Leu His Ile Ala Val Val Asn Gln
    115                 120                 125
```

-continued

```
Asn Met Asn Leu Val Arg Ala Leu Leu Ala Arg Arg Ala Ser Val Ser
    130                 135                 140

Ala Arg Ala Thr Gly Thr Ala Phe Arg Arg Ser Pro Cys Asn Leu Ile
145                 150                 155                 160

Tyr Phe Gly Glu His Pro Leu Ser Phe Ala Ala Cys Val Asn Ser Glu
                165                 170                 175

Glu Ile Val Arg Leu Leu Ile Glu His Gly Ala Asp Ile Arg Ala Gln
                180                 185                 190

Asp Ser Leu Gly Asn Thr Val Leu His Ile Leu Ile Leu Gln Pro Asn
                195                 200                 205

Lys Thr Phe Ala Cys Gln Met Tyr Asn Leu Leu Ser Tyr Asp Arg
    210                 215                 220

His Gly Asp His Leu Gln Pro Leu Asp Leu Val Pro Asn His Gln Gly
225                 230                 235                 240

Leu Thr Pro Phe Lys Leu Ala Gly Val Glu Gly Asn Thr Val Met Phe
                245                 250                 255

Gln His Leu Met Gln Lys Arg Lys His Thr Gln Trp Thr Tyr Gly Pro
                260                 265                 270

Leu Thr Ser Thr Leu Tyr Asp Leu Thr Glu Ile Asp Ser Ser Gly Asp
                275                 280                 285

Glu Gln Ser Leu Leu Glu Leu Ile Ile Thr Thr Lys Lys Arg Glu Ala
    290                 295                 300

Arg Gln Ile Leu Asp Gln Thr Pro Val Lys Glu Leu Val Ser Leu Lys
305                 310                 315                 320

Trp Lys Arg Tyr Gly Arg Pro Tyr Phe Cys Met Leu Gly Ala Ile Tyr
                325                 330                 335

Leu Leu Tyr Ile Ile Cys Phe Thr Met Cys Cys Ile Tyr Arg Pro Leu
                340                 345                 350

Lys Pro Arg Thr Asn Asn Arg Thr Ser Pro Arg Asp Asn Thr Leu Leu
                355                 360                 365

Gln Gln Lys Leu Leu Gln Glu Ala Tyr Met Thr Pro Lys Asp Asp Ile
    370                 375                 380

Arg Leu Val Gly Glu Leu Val Thr Val Ile Gly Ala Ile Ile Ile Leu
385                 390                 395                 400

Leu Val Glu Val Pro Asp Ile Phe Arg Met Gly Val Thr Arg Phe Phe
                405                 410                 415

Gly Gln Thr Ile Leu Gly Gly Pro Phe His Val Leu Ile Ile Thr Tyr
                420                 425                 430

Ala Phe Met Val Leu Val Thr Met Val Met Arg Leu Ile Ser Ala Ser
                435                 440                 445

Gly Glu Val Val Pro Met Ser Phe Ala Leu Val Leu Gly Trp Cys Asn
    450                 455                 460

Val Met Tyr Phe Ala Arg Gly Phe Gln Met Leu Gly Pro Phe Thr Ile
465                 470                 475                 480

Met Ile Gln Lys Met Ile Phe Gly Asp Leu Met Arg Phe Cys Trp Leu
                485                 490                 495

Met Ala Val Val Ile Leu Gly Phe Ala Ser Ala Phe Tyr Ile Ile Phe
                500                 505                 510

Gln Thr Glu Asp Pro Glu Glu Leu Gly His Phe Tyr Asp Tyr Pro Met
                515                 520                 525

Ala Leu Phe Ser Thr Phe Glu Leu Phe Leu Thr Ile Ile Asp Gly Pro
    530                 535                 540

Ala Asn Tyr Asn Val Asp Leu Pro Phe Met Tyr Ser Ile Thr Tyr Ala
```

-continued

```
               545                 550                 555                 560
               Ala Phe Ala Ile Ile Ala Thr Leu Leu Met Leu Asn Leu Leu Ile Ala
                              565                 570                 575
               Met Met Gly Asp Thr His Trp Arg Val Ala His Glu Arg Asp Glu Leu
                         580                 585                 590
               Trp Arg Ala Gln Ile Val Ala Thr Thr Val Met Leu Glu Arg Lys Leu
                         595                 600                 605
               Pro Arg Cys Leu Trp Pro Arg Ser Gly Ile Cys Gly Arg Glu Tyr Gly
                         610                 615                 620
               Leu Gly Asp Arg Trp Phe Leu Arg Val Glu Asp Arg Gln Asp Leu Asn
               625                 630                 635                 640
               Arg Gln Arg Ile Gln Arg Tyr Ala Gln Ala Phe His Thr Arg Gly Ser
                              645                 650                 655
               Glu Asp Leu Asp Lys Asp Ser Val Glu Lys Leu Glu Leu Gly Cys Pro
                         660                 665                 670
               Phe Ser Pro His Leu Ser Leu Pro Met Pro Ser Val Ser Arg Ser Thr
                         675                 680                 685
               Ser Arg Ser Ser Ala Asn Trp Glu Arg Leu Arg Gln Gly Thr Leu Arg
                         690                 695                 700
               Arg Asp Leu Arg Gly Ile Ile Asn Arg Gly Leu Glu Asp Gly Glu Ser
               705                 710                 715                 720
               Trp Glu Tyr Gln Ile
                              725

<210> SEQ ID NO 3
<211> LENGTH: 2955
<212> TYPE: DNA
<213> ORGANISM: Rattus sp.
<220> FEATURE:
<221> NAME/KEY: CDS
<222> LOCATION: (293)..(2476)

<400> SEQUENCE: 3
ccacgcgtcc gcacagctcc tgctcactcc caacaggagc tccgatatac aagcccagca     60
gatttccagc tctgccaagt ggaacaaagc aggagccctc ttcggactcc taagagcagc    120
cacgggaagc tcaccagct ccacaggtga agtaggagga agaacacagg agacgggacc     180
tctacagaga gagggtaggc cggctcttgg ggatgccaat gtggccccag gtcgagccc     240 aggtggggtc tggcatcagc ctcagccccc caaggactca gccttccacc cc atg ggg    298
                                                           Met Gly
                                                             1 tgg tca ctg ccc aag gag aag ggg tta ata ctc tgc cta tgg aac aag      346
Trp Ser Leu Pro Lys Glu Lys Gly Leu Ile Leu Cys Leu Trp Asn Lys
      5                  10                  15 ttc tgc aga tgg ttc cac aga cga gag tcc tgg gct cag agc cga gat      394
Phe Cys Arg Trp Phe His Arg Arg Glu Ser Trp Ala Gln Ser Arg Asp
 20                  25                  30 gag cag aac ctg ctg cag cag aag agg atc tgg gag tcg cct ctt ctt      442
Glu Gln Asn Leu Leu Gln Gln Lys Arg Ile Trp Glu Ser Pro Leu Leu
35                  40                  45                  50 cta gct gcc aaa gaa aac aat gtc cag gct ctg atc aaa ctg ctc aag      490
Leu Ala Ala Lys Glu Asn Asn Val Gln Ala Leu Ile Lys Leu Leu Lys
              55                  60                  65 ttt gaa gga tgt gag gtg cac cag aaa gga gcc atg ggg gaa act gca      538
Phe Glu Gly Cys Glu Val His Gln Lys Gly Ala Met Gly Glu Thr Ala
         70                  75                  80 ctt cac ata gct gcc ctc tat gat aac ctg gag gct gcc atg gtg cta      586
```

```
                    Leu His Ile Ala Ala Leu Tyr Asp Asn Leu Glu Ala Ala Met Val Leu
                            85                  90                  95 atg gag gct gcc cca gaa ctg gtt ttt gag ccc atg act tca gag cta       634
Met Glu Ala Ala Pro Glu Leu Val Phe Glu Pro Met Thr Ser Glu Leu
    100                 105                 110 tat gaa ggt cag act gca ctg cac att gca gta ata aac cag aat gtg       682
Tyr Glu Gly Gln Thr Ala Leu His Ile Ala Val Ile Asn Gln Asn Val
115                 120                 125                 130 aac ttg gtc cgt gct ctg ctt gcc cga ggg gcc agt gtc tcc gcc aga       730
Asn Leu Val Arg Ala Leu Leu Ala Arg Gly Ala Ser Val Ser Ala Arg
            135                 140                 145 gct acg ggc tct gtc ttc cac tac agg cct cac aat ctc att tac tat       778
Ala Thr Gly Ser Val Phe His Tyr Arg Pro His Asn Leu Ile Tyr Tyr
                150                 155                 160 gga gaa cat cct ttg tcc ttt gct gcc tgt gtg ggt agt gag gag att       826
Gly Glu His Pro Leu Ser Phe Ala Ala Cys Val Gly Ser Glu Glu Ile
            165                 170                 175 gtt aga ctg ctc atc gag cat ggg gct gac att cgg gcc cag gac tcc       874
Val Arg Leu Leu Ile Glu His Gly Ala Asp Ile Arg Ala Gln Asp Ser
    180                 185                 190 ttg gga aat aca gta cta cac ata ctc atc ttg cag ccc aac aaa acc       922
Leu Gly Asn Thr Val Leu His Ile Leu Ile Leu Gln Pro Asn Lys Thr
195                 200                 205                 210 ttt gcc tgc cag atg tac aac ctg cta ctg tcc tat gat ggg gga gac       970
Phe Ala Cys Gln Met Tyr Asn Leu Leu Leu Ser Tyr Asp Gly Gly Asp
            215                 220                 225 cac ctg aag tcc ctt gaa ctt gtg ccc aat aac caa gga ctc acc cct      1018
His Leu Lys Ser Leu Glu Leu Val Pro Asn Asn Gln Gly Leu Thr Pro
                230                 235                 240 ttc aag ttg gct ggg gtg gaa ggc aac att gtg atg ttc caa cac ctg      1066
Phe Lys Leu Ala Gly Val Glu Gly Asn Ile Val Met Phe Gln His Leu
            245                 250                 255 atg cag aag cgg aaa cac atc cag tgg act tat ggg cca ttg act tcc      1114
Met Gln Lys Arg Lys His Ile Gln Trp Thr Tyr Gly Pro Leu Thr Ser
    260                 265                 270 aca ctt tat gac ctc act gag att gac tcc tca ggg gat gat caa tct      1162
Thr Leu Tyr Asp Leu Thr Glu Ile Asp Ser Ser Gly Asp Asp Gln Ser
275                 280                 285                 290 cta ctg gaa ctt att gtt acc acc aag aag cgg gag gct cgc cag atc      1210
Leu Leu Glu Leu Ile Val Thr Thr Lys Lys Arg Glu Ala Arg Gln Ile
            295                 300                 305 ctg gac cag aca cct gtg aag gaa ctg gtg agc ctc aag tgg aag agg      1258
Leu Asp Gln Thr Pro Val Lys Glu Leu Val Ser Leu Lys Trp Lys Arg
                310                 315                 320 tat ggg cgg ccc tac ttc tgt gtg ctg ggt gcc atc tac gtg ctc tac      1306
Tyr Gly Arg Pro Tyr Phe Cys Val Leu Gly Ala Ile Tyr Val Leu Tyr
            325                 330                 335 atc atc tgc ttt acc atg tgc tgt gtc tac cgc cca ctc aag ccc agg      1354
Ile Ile Cys Phe Thr Met Cys Cys Val Tyr Arg Pro Leu Lys Pro Arg
    340                 345                 350 atc act aac cgc acc aac ccc agg gac aat acc ctg cag cag aag          1402
Ile Thr Asn Arg Thr Asn Pro Arg Asp Asn Thr Leu Gln Gln Lys
355                 360                 365                 370 ctc ctt cag gag gcc tat gtg acc ccc aag gat gat ctc cgg ctg gtg      1450
Leu Leu Gln Glu Ala Tyr Val Thr Pro Lys Asp Asp Leu Arg Leu Val
            375                 380                 385 ggg gag ctg gtg agc atc gtt ggg gct gtg atc atc ctg ctg gtg gag      1498
Gly Glu Leu Val Ser Ile Val Gly Ala Val Ile Ile Leu Leu Val Glu
    390                 395                 400
```

-continued

| | |
|---|---|
| att cca gac atc ttc agg ttg ggg gtc act cga ttt ttt ggg cag acc<br>Ile Pro Asp Ile Phe Arg Leu Gly Val Thr Arg Phe Phe Gly Gln Thr<br>405                          410                      415 | 1546 |
| att ctt ggg ggg cca ttc cat gtc atc att gtc act tat gcc ttc atg<br>Ile Leu Gly Gly Pro Phe His Val Ile Ile Val Thr Tyr Ala Phe Met<br>    420                      425                      430 | 1594 |
| gtg ctg gtg acc atg gtg atg cgg ctc acc aac tca gat gga gag gtg<br>Val Leu Val Thr Met Val Met Arg Leu Thr Asn Ser Asp Gly Glu Val<br>435                          440                      445                      450 | 1642 |
| gtg ccc atg tcg ttt gct ctg gtg ttg ggc tgg tgc aat gtc atg tac<br>Val Pro Met Ser Phe Ala Leu Val Leu Gly Trp Cys Asn Val Met Tyr<br>                      455                      460                      465 | 1690 |
| ttt gcc aga gga ttc caa atg ctg ggt ccc ttc acc atc atg atc cag<br>Phe Ala Arg Gly Phe Gln Met Leu Gly Pro Phe Thr Ile Met Ile Gln<br>              470                      475                      480 | 1738 |
| aag atg att ttt ggt gac ttg atg cga ttc tgc tgg ctg atg gct gtg<br>Lys Met Ile Phe Gly Asp Leu Met Arg Phe Cys Trp Leu Met Ala Val<br>485                          490                      495 | 1786 |
| gta atc ttg gga ttt gct tca gcc ttc tat atc atc ttc cag aca gag<br>Val Ile Leu Gly Phe Ala Ser Ala Phe Tyr Ile Ile Phe Gln Thr Glu<br>    500                      505                      510 | 1834 |
| gac ccc gat gag ctg ggc cat ttc tat gac tac ccc atg gca ctg ttc<br>Asp Pro Asp Glu Leu Gly His Phe Tyr Asp Tyr Pro Met Ala Leu Phe<br>515                          520                      525                      530 | 1882 |
| agc acc ttt gaa ctc ttc ctc acc atc atc gat ggc cct gcc aac tat<br>Ser Thr Phe Glu Leu Phe Leu Thr Ile Ile Asp Gly Pro Ala Asn Tyr<br>                      535                      540                      545 | 1930 |
| gac gtg gat ctg ccc ttc atg tac agc atc acc tac gct gcc ttt gcc<br>Asp Val Asp Leu Pro Phe Met Tyr Ser Ile Thr Tyr Ala Ala Phe Ala<br>            550                      555                      560 | 1978 |
| atc atc gcc aca ctg ctc atg ctc aac ctc cta att gcc atg atg ggt<br>Ile Ile Ala Thr Leu Leu Met Leu Asn Leu Leu Ile Ala Met Met Gly<br>              565                      570                      575 | 2026 |
| gac act cac tgg aga gtt gcc cat gag cgg gat gag ctc tgg aga gca<br>Asp Thr His Trp Arg Val Ala His Glu Arg Asp Glu Leu Trp Arg Ala<br>580                          585                      590 | 2074 |
| cag gtt gtg gct act acc gtg atg cta gaa cgg aag ctg cct cgc tgc<br>Gln Val Val Ala Thr Thr Val Met Leu Glu Arg Lys Leu Pro Arg Cys<br>595                          600                      605                      610 | 2122 |
| ctg tgg cct cga tct ggg ata tgt ggg cga gag tat ggt ctt ggg gac<br>Leu Trp Pro Arg Ser Gly Ile Cys Gly Arg Glu Tyr Gly Leu Gly Asp<br>                      615                      620                      625 | 2170 |
| cgc tgg ttc ttg agg gtg gaa gat aga caa gat ctc aac aga caa cgc<br>Arg Trp Phe Leu Arg Val Glu Asp Arg Gln Asp Leu Asn Arg Gln Arg<br>            630                      635                      640 | 2218 |
| atc cgc cgc tat gca cag gcc ttc cag caa caa gat gac ctc tac tct<br>Ile Arg Arg Tyr Ala Gln Ala Phe Gln Gln Gln Asp Asp Leu Tyr Ser<br>              645                      650                      655 | 2266 |
| gag gac ttg gaa aaa gac tca gga gaa aaa ctg gag atg gca cga ccc<br>Glu Asp Leu Glu Lys Asp Ser Gly Glu Lys Leu Glu Met Ala Arg Pro<br>            660                      665                      670 | 2314 |
| ttt ggt gcc tat ctg tcc ttt cct aca ccc tca gtg tct cga agt acc<br>Phe Gly Ala Tyr Leu Ser Phe Pro Thr Pro Ser Val Ser Arg Ser Thr<br>675                          680                      685                      690 | 2362 |
| tcc cga agc agc acc aat tgg gac agg ctt cga caa ggg gcc cta agg<br>Ser Arg Ser Ser Thr Asn Trp Asp Arg Leu Arg Gln Gly Ala Leu Arg<br>              695                      700                      705 | 2410 |
| aag gac ctt caa ggg ata atc aac cgg ggc ctg gaa gat ggg gag ggc<br>Lys Asp Leu Gln Gly Ile Ile Asn Arg Gly Leu Glu Asp Gly Glu Gly<br>            710                      715                      720 | 2458 |

```
tgg gag tac cag atc taa atgttggctc tcaccaaaca tcaaaacaga          2506
Trp Glu Tyr Gln Ile
        725 atgaaagaaa accagttcaa aactagaagt catcctgcaa gtccaaggag aagggggagg  2566 aacatgctaa ggaatgtaca ataaatcctt cagagctcca caactccacc ttggggcaga  2626 aagaagaaga ttctgtggtc cttgcctcaa ccaagcattc cttgttctct tatggaagct  2686 ccctgcaca ccagagcact taaagacag gcttcccgtc acaggcacct gtctccaccc    2746 aggtctaata agtgggaggg cacagaactc tacccagagt gcttcagagg accggtggag  2806 aacactcaga ttgtgggaaa gcgtgtgatg gagagataca ggcaccagtc tagggtgggt  2866 gaaactaggc tgagccttgc caccttccag taaagtcatt tcctgatccc caaaaaaaaa  2926 aaaaaaaaaa aaaaaaaaaa aaaaaaaaa                                    2955
```

<210> SEQ ID NO 4
<211> LENGTH: 727
<212> TYPE: PRT
<213> ORGANISM: Rattus sp.

<400> SEQUENCE: 4

```
Met Gly Trp Ser Leu Pro Lys Glu Lys Gly Leu Ile Leu Cys Leu Trp
1               5                   10                  15

Asn Lys Phe Cys Arg Trp Phe His Arg Arg Glu Ser Trp Ala Gln Ser
                20                  25                  30

Arg Asp Glu Gln Asn Leu Leu Gln Gln Lys Arg Ile Trp Glu Ser Pro
            35                  40                  45

Leu Leu Leu Ala Ala Lys Glu Asn Asn Val Gln Ala Leu Ile Lys Leu
        50                  55                  60

Leu Lys Phe Glu Gly Cys Glu Val His Gln Lys Gly Ala Met Gly Glu
65                  70                  75                  80

Thr Ala Leu His Ile Ala Ala Leu Tyr Asp Asn Leu Glu Ala Ala Met
                85                  90                  95

Val Leu Met Glu Ala Ala Pro Glu Leu Val Phe Glu Pro Met Thr Ser
                100                 105                 110

Glu Leu Tyr Glu Gly Gln Thr Ala Leu His Ile Ala Val Ile Asn Gln
            115                 120                 125

Asn Val Asn Leu Val Arg Ala Leu Leu Ala Arg Gly Ala Ser Val Ser
        130                 135                 140

Ala Arg Ala Thr Gly Ser Val Phe His Tyr Arg Pro His Asn Leu Ile
145                 150                 155                 160

Tyr Tyr Gly Glu His Pro Leu Ser Phe Ala Ala Cys Val Gly Ser Glu
                165                 170                 175

Glu Ile Val Arg Leu Leu Ile Glu His Gly Ala Asp Ile Arg Ala Gln
                180                 185                 190

Asp Ser Leu Gly Asn Thr Val Leu His Ile Leu Ile Leu Gln Pro Asn
            195                 200                 205

Lys Thr Phe Ala Cys Gln Met Tyr Asn Leu Leu Leu Ser Tyr Asp Gly
        210                 215                 220

Gly Asp His Leu Lys Ser Leu Glu Leu Val Pro Asn Asn Gln Gly Leu
225                 230                 235                 240

Thr Pro Phe Lys Leu Ala Gly Val Glu Gly Asn Ile Val Met Phe Gln
                245                 250                 255

His Leu Met Gln Lys Arg Lys His Ile Gln Trp Thr Tyr Gly Pro Leu
                260                 265                 270
```

```
Thr Ser Thr Leu Tyr Asp Leu Thr Glu Ile Asp Ser Ser Gly Asp Asp
        275                 280                 285

Gln Ser Leu Leu Glu Leu Ile Val Thr Lys Lys Arg Glu Ala Arg
    290                 295                 300

Gln Ile Leu Asp Gln Thr Pro Val Lys Glu Leu Val Ser Leu Lys Trp
305                 310                 315                 320

Lys Arg Tyr Gly Arg Pro Tyr Phe Cys Val Leu Gly Ala Ile Tyr Val
                325                 330                 335

Leu Tyr Ile Ile Cys Phe Thr Met Cys Cys Val Tyr Arg Pro Leu Lys
            340                 345                 350

Pro Arg Ile Thr Asn Arg Thr Asn Pro Arg Asp Asn Thr Leu Leu Gln
        355                 360                 365

Gln Lys Leu Leu Gln Glu Ala Tyr Val Thr Pro Lys Asp Asp Leu Arg
    370                 375                 380

Leu Val Gly Glu Leu Val Ser Ile Val Gly Ala Val Ile Ile Leu Leu
385                 390                 395                 400

Val Glu Ile Pro Asp Ile Phe Arg Leu Gly Val Thr Arg Phe Phe Gly
                405                 410                 415

Gln Thr Ile Leu Gly Gly Pro Phe His Val Ile Ile Val Thr Tyr Ala
            420                 425                 430

Phe Met Val Leu Val Thr Met Val Met Arg Leu Thr Asn Ser Asp Gly
            435                 440                 445

Glu Val Val Pro Met Ser Phe Ala Leu Val Leu Gly Trp Cys Asn Val
    450                 455                 460

Met Tyr Phe Ala Arg Gly Phe Gln Met Leu Gly Pro Phe Thr Ile Met
465                 470                 475                 480

Ile Gln Lys Met Ile Phe Gly Asp Leu Met Arg Phe Cys Trp Leu Met
                485                 490                 495

Ala Val Val Ile Leu Gly Phe Ala Ser Ala Phe Tyr Ile Ile Phe Gln
            500                 505                 510

Thr Glu Asp Pro Asp Glu Leu Gly His Phe Tyr Asp Tyr Pro Met Ala
        515                 520                 525

Leu Phe Ser Thr Phe Glu Leu Phe Leu Thr Ile Ile Asp Gly Pro Ala
    530                 535                 540

Asn Tyr Asp Val Asp Leu Pro Phe Met Tyr Ser Ile Thr Tyr Ala Ala
545                 550                 555                 560

Phe Ala Ile Ile Ala Thr Leu Leu Met Leu Asn Leu Leu Ile Ala Met
                565                 570                 575

Met Gly Asp Thr His Trp Arg Val Ala His Glu Arg Asp Glu Leu Trp
            580                 585                 590

Arg Ala Gln Val Val Ala Thr Thr Val Met Leu Glu Arg Lys Leu Pro
        595                 600                 605

Arg Cys Leu Trp Pro Arg Ser Gly Ile Cys Gly Arg Glu Tyr Gly Leu
    610                 615                 620

Gly Asp Arg Trp Phe Leu Arg Val Glu Asp Arg Gln Asp Leu Asn Arg
625                 630                 635                 640

Gln Arg Ile Arg Arg Tyr Ala Gln Ala Phe Gln Gln Gln Asp Asp Leu
                645                 650                 655

Tyr Ser Glu Asp Leu Glu Lys Asp Ser Gly Glu Lys Leu Glu Met Ala
            660                 665                 670

Arg Pro Phe Gly Ala Tyr Leu Ser Phe Pro Thr Pro Ser Val Ser Arg
        675                 680                 685
```

-continued

```
Ser Thr Ser Arg Ser Ser Thr Asn Trp Asp Arg Leu Arg Gln Gly Ala
        690             695             700

Leu Arg Lys Asp Leu Gln Gly Ile Ile Asn Arg Gly Leu Glu Asp Gly
705             710             715             720

Glu Gly Trp Glu Tyr Gln Ile
                725
```